United States Patent
Otvos et al.

(10) Patent No.: US 11,782,002 B2
(45) Date of Patent: *Oct. 10, 2023

(54) NMR QUANTIFICATION OF TMAO

(71) Applicant: Liposcience, Inc., Morrisville, NC (US)

(72) Inventors: James D. Otvos, Apex, NC (US); Elias J. Jeyarajah, Raleigh, NC (US); Justyna E. Wolak-Dinsmore, Durham, NC (US); Thomas M. O'Connell, Chapel Hill, NC (US); Dennis W. Bennett, Shorewood, WI (US); Steven P. Matyus, Durham, NC (US); Stanley L. Hazen, Pepper Pike, OH (US)

(73) Assignee: LipoScience, Inc., Morrisville, NC (US)

( * ) Notice: Subject to any disclaimer, the term of this patent is extended or adjusted under 35 U.S.C. 154(b) by 641 days.

This patent is subject to a terminal disclaimer.

(21) Appl. No.: 16/813,136

(22) Filed: Mar. 9, 2020

(65) Prior Publication Data

US 2020/0355634 A1 Nov. 12, 2020

Related U.S. Application Data

(63) Continuation of application No. 15/364,618, filed on Nov. 30, 2016, now Pat. No. 10,613,044, which is a
(Continued)

(51) Int. Cl.
*G01N 33/48* (2006.01)
*G01N 33/50* (2006.01)
(Continued)

(52) U.S. Cl.
CPC .......... *G01N 24/08* (2013.01); *G01N 24/088* (2013.01); *G01N 33/66* (2013.01); *G01R 33/465* (2013.01);
(Continued)

(58) Field of Classification Search
CPC ...... G01N 24/08; G01N 24/088; G01N 33/66; G01N 2800/323; G01R 33/465; G16B 5/00; G16B 45/00
See application file for complete search history.

(56) References Cited

U.S. PATENT DOCUMENTS

| 4,529,710 A | 7/1985 | Spicer et al. |
| 7,243,030 B2 | 7/2007 | Reeve et al. |

(Continued)

FOREIGN PATENT DOCUMENTS

WO   WO 2008/020416   2/2008

OTHER PUBLICATIONS

Baryshnikova et al. Internal pH indicators for biomolecular NMR. Journal of Biomolecular NMR, vol. 41, pp. 5-7. (Year: 2008).*

(Continued)

*Primary Examiner* — Russell S Negin
(74) *Attorney, Agent, or Firm* — Kilpatrick Townsend & Stockton LLP

(57) ABSTRACT

A defined peak region residing between about 3.2 and 3.4 ppm of a proton NMR spectrum of an in vitro biosample is electronically evaluated to determine a level of trimethylamine-N-oxide ("TMAO"). The biosamples may be any suitable biosamples including human serum with a normal biologic range of between about 1-50 µM or urine with a normal biologic range of between about 0-1000 µM.

19 Claims, 22 Drawing Sheets

Related U.S. Application Data continuation of application No. 14/404,858, filed as application No. PCT/US2013/041274 on May 16, 2013, now Pat. No. 9,541,620, and a continuation-in-part of application No. 13/801,604, filed on Mar. 13, 2013, now Pat. No. 9,535,144.

(60) Provisional application No. 61/654,249, filed on Jun. 1, 2012, provisional application No. 61/654,249, filed on Jun. 1, 2012.

(51) Int. Cl.
| | |
|---|---|
| *G01N 24/08* | (2006.01) |
| *G01R 33/465* | (2006.01) |
| *G01N 33/66* | (2006.01) |
| *G16B 5/00* | (2019.01) |
| *G16B 45/00* | (2019.01) |

(52) U.S. Cl.
CPC .............. *G16B 5/00* (2019.02); *G16B 45/00* (2019.02); *G01N 2800/323* (2013.01)

(56) References Cited

U.S. PATENT DOCUMENTS

| | | | |
|---|---|---|---|
| 9,535,144 | B2 | 1/2017 | Otvos et al. |
| 9,541,620 | B2 | 1/2017 | Otvos et al. |
| 10,613,044 | B2 * | 4/2020 | Otvos ................ G16B 5/00 |
| 2004/0058386 | A1 | 3/2004 | Wishart et al. |
| 2005/0074745 | A1 | 4/2005 | Clayton et al. |
| 2008/0183101 | A1 | 7/2008 | Stonehouse et al. |
| 2010/0285517 | A1 | 11/2010 | Hazen et al. |
| 2011/0295517 | A1 | 12/2011 | Otvos et al. |
| 2015/0149094 | A1 | 5/2015 | Otvos et al. |

OTHER PUBLICATIONS

Beckonert et al., Metabolic profiling, metabolomics and metabonomic procedures for NMR spectroscopy of urine, plasma, serum and tissue extracts, Nature Protocols, 2007, pp. 2692-2703, vol. 2, No. 11.

Bell J. et al., "Nuclear magnetic resonance studies of blood plasma and urine from subjects with chronic renal failure: identification of trimethylamine-N-oxide",Biochimica et Biophysica Acta. Molecular Basis and Disease, Amsterdam, NL, vol. 1096, No. 2, 1991, pp. 101-107.

Bertini et al., The Metabonomic Signature of Celiac Disease, Journal of Proteome Research, 2009, pp. 170-177, vol. 8.

Delaglio et al., Measurement of homonuclear proton couplings from regular 2D COSY spectra. Journal of Magnetic Resonance, vol. 149, 2001, pp. 276-281.

European Patent Office, Extended European Search Report, Application No. 13798148 dated Feb. 8, 2016.

Ijare O. et al., "The Effect of pH on the Analysis of 1 H MRS Data of Urine in Biomedical Applications", Proceedings of the International Society for Magnetic Resonance in Medicine, 17th Scientific Meeting and Exhibition, 2009, p. 4302.

Janssens et al., Evaluation in three zero-area digital filters for peak recognition and interference detection in automated spectral data analysis, Analytical Chemistry, vol. 63, 1991, p. 320-331.

Ogg et al., WET, a $T^1$- and $B^1$-Insensitive Water-Suppression Method for in Vivo Localized $^1H$ NMR Spectroscopy, Journal of Magnetic Resonance, Abstract, May 1, 1994, pp. 1-10, vol. 104, Issue 1.

Otvos et al., Quantification of Plasma Lipoproteins by Proton Nuclear Magnetic Resonance Spectroscopy, Clinical Chemistry, 1991, pp. 377-386, vol. 37, No. 3.

Patent Cooperation Treaty, International Preliminary Report on Patentability, International Application No. PCT/US2013/041274, dated Dec. 2, 2014.

Patent Cooperation Treaty, International Search Report and Written Opinion, International Application No. PCT/US2013/041274, dated Sep. 10, 2013.

Pauli, G.et al., "Quantitative 1 H NMR. Development and Potential of an Analytical Method: An Update", Journal of Natural Products vol. 75, No. 4, 2012, pp. 834-851.

Rak et al., The diet-microbe morbid union, Nature, Apr. 7, 2011, pp. 40-41, vol. 472.

Simpson et al., Purge NMR: Effective and easy solvent suppression, Journal of Magnetic Resonance, Abstract, Aug. 2005, pp. 340-346, vol. 175, Issue 2.

U.S. Appl. No. 13/801,604, Non-Final Office Action, dated Apr. 28, 2015.

U.S. Appl. No. 13/801,604, Supplemental Non-Final Office Action, dated May 4, 2015.

Wang et al., Gut flora metabolism of phosphatidylcholine promotes cardiovascular disease, Nature, Apr. 7, 2011, pp. 57-65 (with supplementary information, additional 46 pages), vol. 472.

Wevers R. et al., "Identification of dihydropyrimidine amidohydrolase deficiency and trimethylaminuria by 1 H•NMR Spectroscopy in body fluids", Proceedings of the International Society for Magnetic Resonance in Medicine, 1994.

Woodham R. et al., "NMR Studies of Human Plasma and Urine: Chronic Renal Failure and Amine Metabolism", Proceedings of the International Society for Magnetic Resonance in Medicine, 8th Annual Meeting and Exhibition, 1989.

* cited by examiner

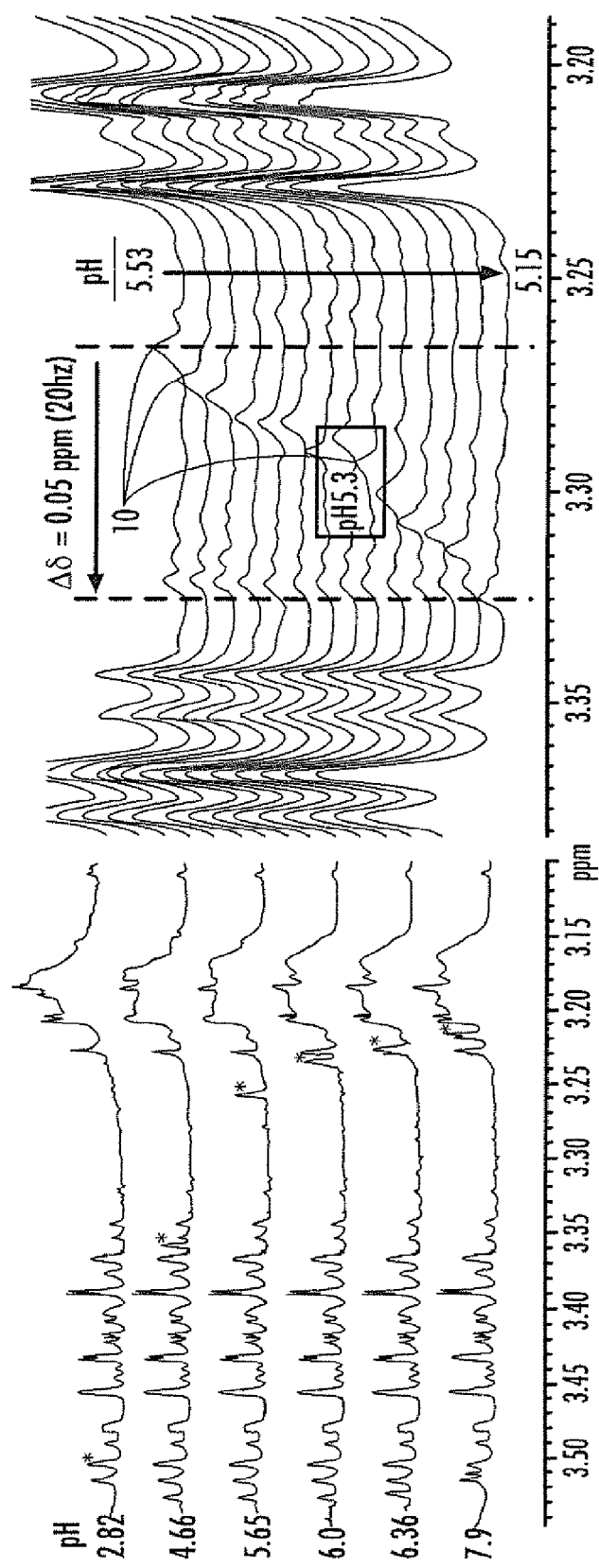

SERUM SAMPLE WITH GLUCOSE REFERENCE SPECTRUM BELOW GLUCOSE MULTIPLET AT 5.2 ppm, THERE ARE MULTIPLETS CENTERED AT 4.6, 3.9, 3.8, 3.7, 3.5, 3.4 AND 3.2 ppm FITTING OF PATIENT TMAO PEAKS WITH CONCENTRATIONS IN THE 1ST (A-B), 2ND (C-D) AND 3RD (E-F) QUARTILES.

Assay performance (%CV) with spiked dialyzed serum with 64, 128 and 192 scans.

FIGURE 12. ASSAY PERFORMANCE (%CV) WITH (A) SPIKED DIALYZED SERUM AND (B) PATIENT SAMPLES.

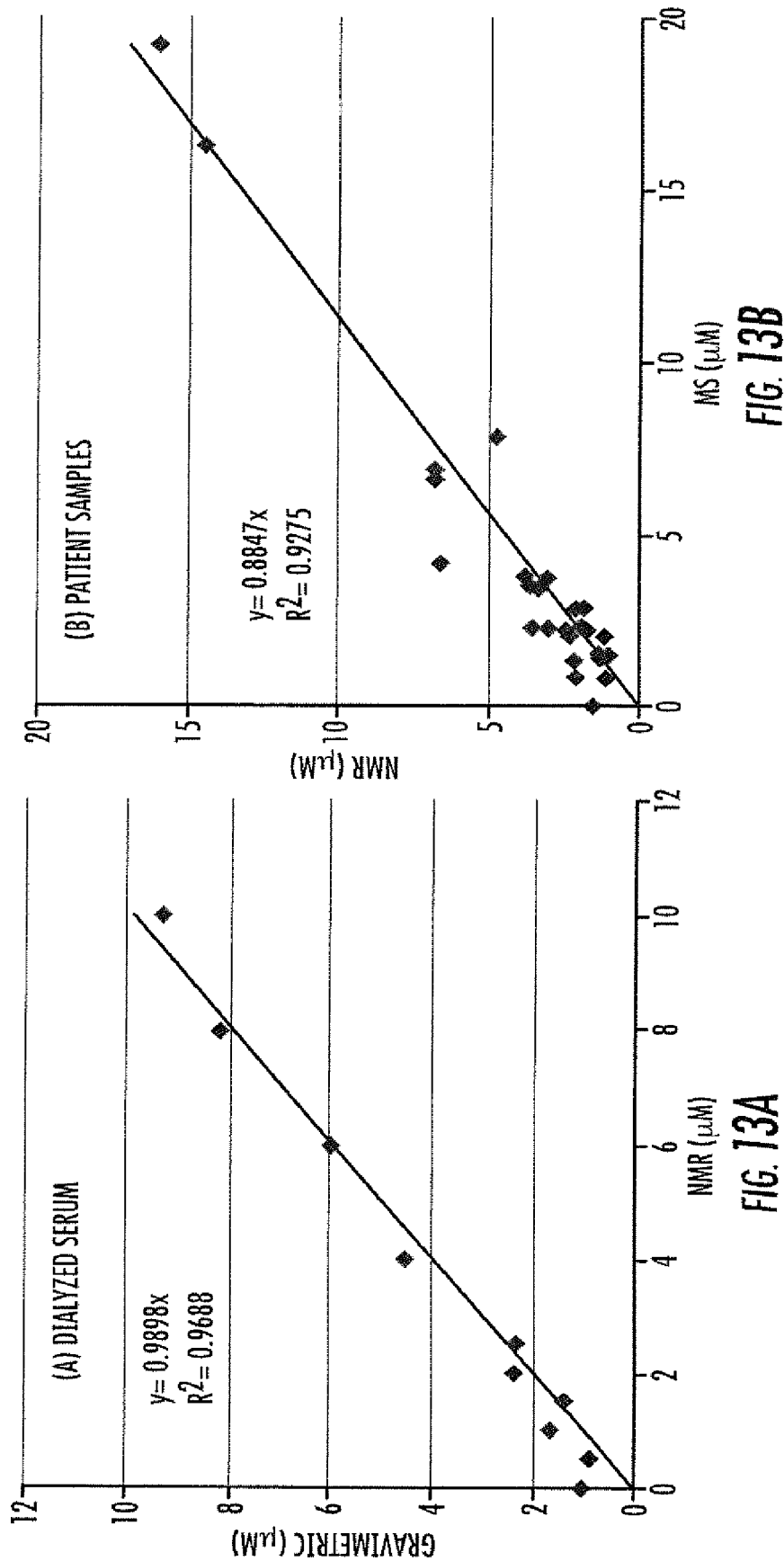
FIGURE 13. COMPARISON OF NMR DETERMINATION OF TMAO (A) IN DIALYZED SERUM WITH GRAVIMENTRALLY DETERMINED TMA AND (B) IN PATIENT SAMPLES WITH MS DETERMINED TMAO

NMR QUANTIFICATION OF TMAO

RELATED APPLICATIONS

This application is a continuation of and claims benefit under 35 U.S.C. § 120 of U.S. application Ser. No. 15/364,618, filed Nov. 30, 2016, which is a continuation of U.S. application Ser. No. 14/404,858, filed Dec. 1, 2014, which is a continuation-in-part of U.S. application Ser. No. 13/801,604, filed Mar. 13, 2013, and corresponding PCT/US13/41274, filed May 16, 2013, which claim the benefit of and priority to U.S. Provisional Application Ser. No. 61/654,249, filed Jun. 1, 2012, the contents of which are all hereby incorporated in their entirety by reference as though fully set forth herein.

FIELD OF THE INVENTION

The present invention relates generally to analysis of in vitro biosamples. The invention may be particularly suitable for NMR analysis of human urine, blood plasma and serum.

BACKGROUND OF THE INVENTION

Researchers have described the use of trimethylamine containing compounds, and in particular trimethylamine-N-oxide ("TMAO" or "TMANO"), as risk predictors for cardiovascular disease. See, U.S. Patent Application Publication 2010/0285517 and Wang et al, *Gut flora metabolism of phosphatidylcholine promotes cardiovascular disease*, Nature, Vol. 472, pp. 57-63 (April, 2011), the contents of which are hereby incorporated by reference as if recited in full herein.

SUMMARY

Embodiments of the invention provide methods, systems, circuits, analyzers and computer program products for NMR quantification of TMAO.

Embodiments of the invention are directed to methods of determining a measure of TMAO in in vitro biosamples. The methods include electronically determining a level of trimethylamine-N-oxide ("TMAO") of an in vitro biosample using a defined TMAO peak region having a single TMAO peak residing between about 3.2 and 3.4 ppm of a proton NMR spectrum.

The method may also include: (a) electronically identifying a defined pH-stable reference peak region in the NMR spectrum of the biosample; (b) electronically identifying a defined calibration peak region in the NMR spectrum of the biosample (the calibration peak region location changes based on pH of the biosample); and (c) electronically calculating a distance between the reference and calibration peak regions; then (d) electronically determining a location of a TMAO peak for the defined TMAO peak region based on the calculated distance.

The electronic determination of the TMAO peak region location can be carried out using a defined relationship of a location of the reference peak region to the calibration peak region with a location of the TMAO peak.

The method can include, before the determining step, calculating a position of a TMAO peak region using a fitting region having first size between about 50-100 data points based on a location of a citrate reference peak or peaks, then reducing the fitting region to about 30 data points centered about the calculated location of the TMAO peak, and electronically curve fitting the TMAO peak region with a defined curve fitting function or functions.

The defined TMAO peak can be at about 3.3 ppm. The electronic determination of the level of TMAO can be carried out by identifying an expected TMAO peak location using a defined (e.g., linear or other) relationship between a location of a reference peak or peaks and a location of a pH sensitive calibration peak or peaks, and location of an expected TMAO peak. A probable actual TMAO peak location can be identified by: first electronically weighting a region around the expected TMAO peak location with a defined function; then electronically identifying a highest weighted data point of the weighted region; then electronically identifying a probable actual TMAO peak location corresponding to location of the highest weighted data point.

The method can include, after the identification of the probable actual TMAO peak location, applying a curve fitting function or functions to a curve fitting region of about 30 to about 50 data points centered about the identified probable actual TMAO peak location to determine the level of TMAO.

The curve fitting function or functions can be configured to selectively allow for one or more neighbors on either side of the probable actual TMAO peak location to account for small misalignments to determine the level of TMAO.

The method can also include: (a) electronically identifying a defined calibration peak multiplet with peaks that vary in distance apart from one another based on pH of the biosample; (b) determining at least one distance between one or more of the peaks in the calibration peak multiplet; (c) electronically determining a pH of the biosample based on the at least one determined distance; then (d) electronically determining a location of a TMAO peak for the defined TMAO peak region based on the determined pH and/or the at least one distance.

The calibration peak multiplet can be a citrate quartet. The electronic curve fitting of the defined peak region with a defined curve fitting function or functions that can be applied to selectively use, zero, one, two or three peak neighbors of the TMAO peak to determine the level of TMAO.

Determining the measure of TMAO can be carried out to generate a measurement that is substantially linear in a typical biological range of between about 1-50 µM, and may be provided in a lower range of between about 1-10 µM (for blood plasma or serum). Larger ranges may be used for other biosamples, such as between about 0-1000 µM for urine.

The reference peak region can be a glucose peak region. The reference glucose peak region can be associated with anomeric glucose at about 5.20 ppm.

The calibration peak region can be associated with one or more peaks of a citrate peak multiplet (e.g., quartet).

The biosample can be a human blood plasma or serum sample. The biosample can include an acidic pH buffer so that the biosample has a pH between about 5.15 and 5.53.

The calibration peak region can be associated with anomeric glucose at about 5.20 ppm and the reference peak region can include one peak of the citrate multiplet (centered) at about 3.7 ppm.

The method may also include: (i) providing containers holding respective biosamples with a solution of citrate acid and sodium dibasic phosphate in a defined ratio, with the pH being between about 5.15 and 5.53; (ii) positioning a respective biosample in an NMR probe of an NMR spectrometer; and (iii) obtaining NMR signal to generate the NMR proton spectrum for determining the level of TMAO.

The electronic determination can be carried out by applying curve fitting functions NMR signal associated with the TMAO peak to determine a first level of TMAO, then subtracting a known concentration of the TMAO standard that was added to the biosample to generate a patient-specific level of TMAO.

The ratio of the solution can be between 25:75 to about 50:50 (buffer:serum) by volume, but other ratios can be used.

In some embodiments, the method may include (i) providing containers holding small volumes (e.g., about 50 μL or less) of respective biosamples with a solution of citrate acid and sodium dibasic phosphate in a defined ratio with the pH being between about 5.15 and 5.53.

The biosample can be human serum and the obtaining step can be carried out with and acquisition time (on average) of about 4 seconds per scan with a plurality of scans per biosample (typically≥16 scans, and more typically≥about 96 scans per biosample, with between about 3-7 minutes, on average, of total acquisition time per biosample).

The method can include generating an output of the level of TMAO with an indication of whether the level is considered normal, high or low and/or with visual (graphic and/or numerical) indicia of a continuum of risk (e.g., a color graphic of increased risk and/or a TMAO risk score going from low to high), and indicating whether a subject is at risk of a complication of atherosclerotic cardiovascular disease, and wherein a subject whose TMAO is above a value associated with a defined—percentile of a reference population is at risk of experiencing a complication of atherosclerotic cardiovascular disease. It is anticipated that the at-risk population would be at or above about the $75^{th}$ or about the $80^{th}$ percentile.

Other embodiments are directed to computer program products for evaluating in vitro biosamples. The computer program product includes a non-transitory computer readable storage medium having computer readable program code embodied in the medium. The computer-readable program code includes computer readable program code that evaluates NMR signal in a defined peak region residing between about 3.2 and 3.4 of a proton NMR spectrum of an in vitro biosample to determine a level of trimethylamine-N-oxide ("TMAO").

The computer program product can also include: computer readable program code that identifies a pH-stable reference peak region in the NMR spectrum of the biosample; computer readable program code that identifies a defined calibration peak region in the NMR spectrum of the biosample; computer readable program code that calculates a distance between the reference and calibration peak regions; and computer readable program code that determines a position of a TMAO peak region to use as the defined peak region to determine the level of TMAO based on the calculated reference and calibration peak region distance.

The computer program code that determines the position of the TMAO peak region can include computer program code that uses a defined relationship of a location of the reference peak to the calibration peak and the calibration peak to the location of the TMAO peak, wherein the calibration and TMAO peak region locations vary according to pH of the biosample.

The computer program product can also include computer readable program code that applies a defined curve fitting function to the defined peak region using at least one neighbor peak to the defined TMAO peak to determine the level of TMAO.

The computer program product that evaluates the NMR signal is configured to generate measurements that are substantially linear in a biological range of between about 1-1000 μM.

The calibration peak region can be associated with glucose at about 5.20 ppm, wherein the reference peak region is for a single peak of a citrate multiplet peak region at about 3.7 ppm.

The computer readable program code that evaluates the TMAO peak region to determine the level of TMAO can include: (a) computer readable program code that weights a region around an expected TMAO peak location with a defined function; (b) computer readable program code that identifies a highest weighted data point of the weighted region as a probable actual TMAO peak location; and (c) computer readable program code that applies a curve fitting function or functions to a curve fitting region of about 30 to about 50 data points centered about the identified probable actual TMAO peak location to determine a level of TMAO.

The computer program code that applies the curve fitting function or functions can selectively allow for one or more neighbors on either side of the probable actual TMAO peak location to account for small misalignments to determine the level of TMAO.

Still other embodiments are directed to an analysis system. The system includes an NMR spectrometer (at least one) for acquiring at least one NMR spectrum of an in vitro biosample; and at least one processor in communication with the NMR spectrometer, the at least one processor configured to determine a level of trimethylamine-N-oxide ("TMAO") in the biosample using the at least one proton NMR spectrum based on a defined peak region residing between about 3.2 and 3.4 of the at least one proton NMR spectrum.

The at least one processor can be configured to (i) identify a pH-stable reference peak region in the at least one NMR spectrum of the biosample; (ii) identify a defined calibration peak region in the at least one NMR spectrum of the biosample; (iii) calculate a distance between the reference and calibration peak regions; then (iv) determine a location of a TMAO peak region for the defined peak region based on the calculated distance.

The TMAO peak location can be determined using a defined relationship of a location of the calibration peak with a location of the TMAO peak, both of which vary according to pH of the biosample, relative to the distance between the calibration and reference peak regions.

The defined TMAO peak region can be at about 3.30 ppm.

The at least one processor can be configured to apply a curve fitting function to the defined peak region using at least one adjacent peak neighbor to the TMAO peak to determine the level of TMAO.

The at least one processor can be configured to generate measurements that are substantially linear in a biological range for expected or normal biological values. The blood plasma or serum range can be between about 1-50 μM, more typically between about 1-10 μM. The urine range can be between about 0-1000 μM.

The reference peak region can be associated with anomeric glucose at about 5.20 ppm, and the calibration peak region can be associated with one or more peaks of a citrate peak multiplet.

The system can also include containers holding respective biosamples with a solution of citrate acid and sodium dibasic phosphate in a defined ratio, the ratio being between 25:75 to about 50:50 (buffer:serum) by volume, with the pH being between about 5.15 and 5.53. The respective containers or just the respective sample in a flow cell are held in the NMR probe for under 4 seconds of acquisition time per scan with a plurality of scans to generate the NMR signal for the respective at least one NMR spectrum.

The at least one processor can be configured to identify an expected TMAO peak location using a defined relationship between a location of a reference peak or peaks and a location of a pH sensitive calibration peak or peaks, and location of an expected TMAO peak. The at least one processor can be configured to identify a probable actual TMAO peak location by (i) weighting a region around the expected TMAO peak location with a defined function; then (ii) identify a highest weighted data point of the weighted region as the probable actual TMAO peak location.

The defined relationship can be a defined linear relationship.

The at least one processor can be configured to apply a curve fitting function or functions to a curve fitting region of about 30 to about 50 data points centered about the identified probable actual TMAO peak location to determine the level of TMAO.

The at least one processor can be configured to apply the curve fitting function or functions to selectively allow for one or more neighbors on either side of the probable actual TMAO peak location to account for small misalignments to determine the level of TMAO.

Further features, advantages and details of the present invention will be appreciated by those of ordinary skill in the art from a reading of the figures and the detailed description of the preferred embodiments that follow, such description being merely illustrative of the present invention. Features described with respect with one embodiment can be incorporated with other embodiments although not specifically discussed therewith. That is, it is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. The foregoing and other aspects of the present invention are explained in detail in the specification set forth below.

As will be appreciated by those of skill in the art in light of the present disclosure, embodiments of the present invention may include methods, systems, apparatus and/or computer program products or combinations thereof.

BRIEF DESCRIPTION OF THE FIGURES

FIG. 2A shows a stacked plot of NMR spectra showing the change in the location of the TMAO peak (indicated by the asterisk) changes with changes in the sample pH according to embodiments of the present invention. FIG. 2B is an expansion of a stacked plot of NMR spectra showing the changes in the TMAO peak location across a narrow pH range from 5.15 to 5.53 according to embodiments of the present invention. Across this range the TMAO peak moves by about 20 Hertz (0.05 ppm at about 400 MHz).

FIGS. 6A and 6B illustrate concentrations in an estimated $1^{st}$ quartile. FIGS. 6C and 6D correspond to measurements in an estimated $2^{nd}$ quartile. FIGS. 6E and 6F correspond to measurements in an estimated 4th quartile.

FIG. 13A is a graph of the correlation between the NMR determined TMAO concentrations (μM) in dialyzed serum spiked with known concentrations of TMAO (μM). The ordinate of the graph indicates the TMAO concentration bases on gravimetrically determined spiking of the dialyzed plasma. The abscissa indicates the NMR measurement of the concentration.

FIG. 13B is a graph of correlation between the NMR determined TMAO concentrations (μM) and those determined by hyphenated liquid-chromatography mass spectrometry measurements (μM) in patient samples to assess accuracy of the assay according to embodiments of the present invention.

FIG. 21 shows a set of the functions with constant height and differential linewidths Quadratic and linear functions are included to model baseline offsets.

Figure 1A:
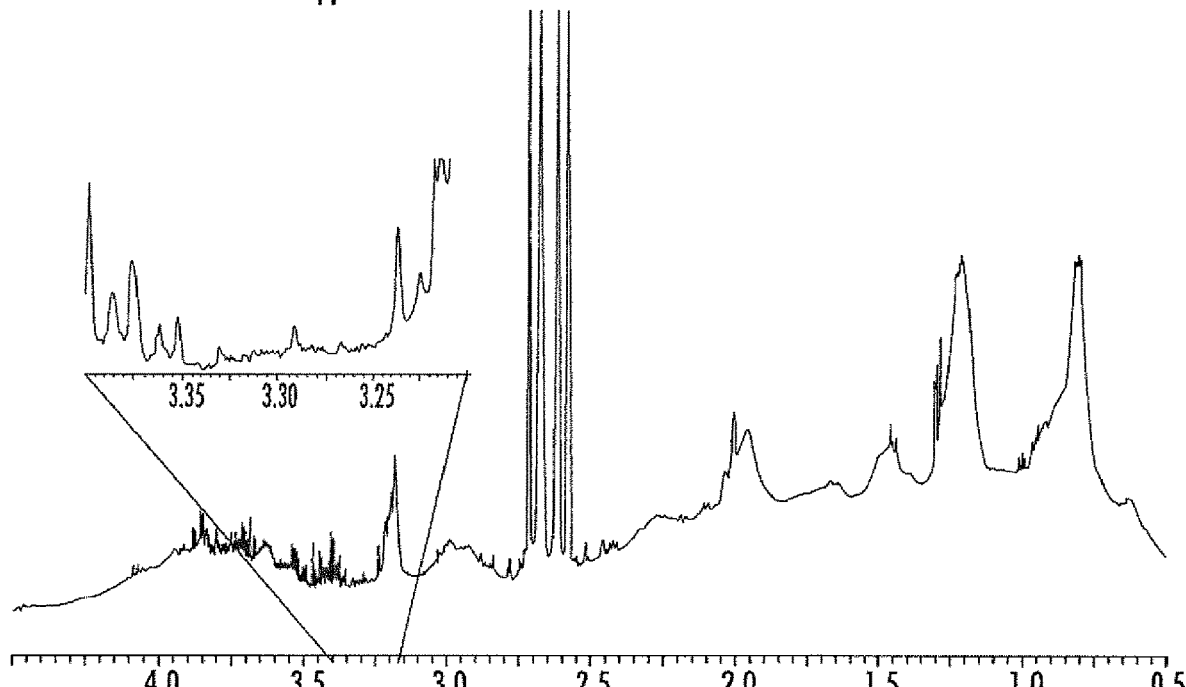
FIG. 1A is an NMR spectrum of human serum with an expansion of the spectrum showing a location of an NMR peak region for TMAO according to embodiments of the present invention.

The foregoing and other objects and aspects of the present invention are explained in detail in the specification set forth below.

DETAILED DESCRIPTION OF EMBODIMENTS OF THE INVENTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Generally stated, embodiments of the invention are directed to NMR assays that can measure the concentration of TMAO in biosamples, typically urine, serum or plasma samples. The concentration can be measured by determining the peak area of a defined region in the NMR proton spectra of the NMR signal and translating this into concentration units of micromoles (μmol) with a calibration based on TMAO standard solutions. The concentration of TMAO in the sample can be related to the subject's risk of developing cardiovascular disease and may also be associated with other diseases or pathologies.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "programmatically" means carried out using computer program and/or software, processor or ASIC directed operations. The term "electronic" and derivatives thereof refer to automated or semi-automated operations carried out using devices with electrical circuits and/or modules rather than via mental steps and typically refers to operations that are carried out programmatically. The terms "automated" and "automatic" means that the operations can be carried out with minimal or no manual labor or input. The term "semi-automated" refers to allowing operators some input or activation, but the calculations and signal acquisition as well as the calculation of the concentrations of the ionized constituent(s) are done electronically, typically programmatically, without requiring manual input.

The term "about" refers to +/−10% of a specified value or number (which can the mean or average value). The term "about" with respect to a chemical shift ppm value for a particular peak location means +/−0.1 as chemical shifts can change with different sample conditions (e.g. salt and protein concentration, etc.).

The terms "CAD" and "CHD" are used interchangeably to correspond to a patient or subject's risk of developing or having coronary artery and/or coronary heart disease, respectively. The term "cardiovascular disease" (CVD) refers to a combined outcome that is typically CHD plus stroke.

The term "biosample" refers to in vitro blood, serum, urine, CSF, saliva, bronchoalveolar lavage, fecal or tissue samples of humans or animals. The biosamples can be from any target subject. Subjects, according to the present invention, can be any animal subject, and are preferably mammalian subjects (e.g., humans, canines, felines, bovines, caprines, ovines, equines, rodents (mice, rats, hamsters, guinea pigs or others), porcines, primates, monkeys, and/or lagomorphs). The animals can be laboratory animals or non-laboratory animals, whether naturally occurring, genetically engineered or modified, and/or whether being laboratory altered, lifestyle and/or diet altered or drug treated animal variations. Embodiments of the invention may be particularly suitable for evaluating human urine and/or human blood plasma or serum biosamples. The samples may be fasting or non-fasting. In some embodiments, the urine and/or blood plasma or serum sample is a fasting sample, at least about 12 hours of fasting time. In other embodiments, the sample can be obtained after a prescribed diet challenge.

The term "patient" is used broadly and refers to an individual that provides a biosample for testing or analysis.

The NMR analysis can be carried out using a small sample size, typically about 500 μL or less, such as between about 100-250 μL. The samples can be diluted with a defined diluent, such as a pH-changing buffer or buffers.

The term "exponential function" refers to a mathematical transformation in which the "FID" is multiplied by an exponential function. Typically decaying exponentials are used to provide a defined increase in the linewidth with commensurate increase in signal-to-noise. The term "FID" refers to free induction decay. The time-domain signal is detected and digitized by the spectrometer after application of the read pulse. Gaussian Multiplication refers to a mathematical transformation in which the FID is multiplied by a Gaussian function in order to narrow the linewidths and increase resolution.

The term "linearity" refers to the ability (within a given range) to provide results that are directly proportional to the concentration of the analyte (here TMAO) in the test sample. The term "limit of detection" ("LoD") refers to the lowest actual concentration at which the analyte is reliably detected. The term "limit of quantification" ("LoQ") refers to the lowest actual concentration at which the analyte is reliably detected (LoD) and at which the uncertainty of the observed results is less than or equal to the error set for uncertainty. The term "precision" refers to the closeness of agreement between independent test results obtained under stipulated conditions.

The term "WET" refers to a solvent suppression scheme in which a series of radiofrequency and pulsed field gradients are used to reduce the water signal. See, Ogg, R. J.; Kingsley, R. B.; Taylor, J. S. J. Magn. Reson., Ser. B 1994, 104, 1-10; and Smallcombe, S. H.; Patt, S. L.; Keifer, P. A. J. Magn. Reson., Ser. A 1995, 117, 295-303, the contents of which are hereby incorporated by reference as if recited in full herein.

The term "CPMG" refers to a Carr-Purcel-Meiboom-Gill pulse sequence. This is a series of phase defined radiofrequency pulses that provide means to attenuate signals from large, rapidly relaxing molecules such as proteins and lipoprotein particles.

The term "AT" refers to acquisition time associated with the length of time that the FID is digitized in seconds. The term "D1" refers to a component of a pulse sequence denoting the delay time prior to the read pulse. The term "Ernst Angle" refers to a read pulse angle for a particular resonance that yields the maximum signal in a given amount of time.

The term "clinical" with respect to data measurements means qualitative and/or quantitative measurements that can be used for therapeutic or diagnostic purposes, and typically for diagnostic purposes and meets the appropriate regulatory guidelines for accuracy, depending on the jurisdiction or test being performed.

Embodiments of the invention can measure TMAO by NMR over an expected biological range of between about 1 to 50 μM, typically 1-30 μM, and more typically about 1-10 μM, for human plasma and/or serum samples. The NMR assay may quantify other expected biological ranges for other sample types, such as urine, for example, which may have an increased amount of TMAO over plasma or serum. The urine range may be much larger than the range for human plasma and/or serum such as between 0-1000 μM. The assay can be linear over the larger urine range of values.

The term "pH buffer" refers to a chemical added to the biosample to create a defined pH-induced NMR peak shift in the NMR spectrum. The buffer can be any suitable acidic buffer such as acetate and/or citrate. As will be discussed below, one particularly suitable buffer is citrate phosphate buffer (e.g., citric acid and sodium dibasic phosphate, e.g., $C_6H_8O_7 \cdot H_2O$ and $Na_2HPO_4 \cdot 7H_2O$).

Embodiments of the invention provide an NMR assay with sufficient accuracy, precision and linearity to provide clinically beneficial measures of TMAO.

It is understood that the chemical shift described herein for NMR signals and peaks are with respect to a spectrometer having an operating frequency of about 400 Hz. As is well-known, peak locations measured in ppm should remain constant at different field strengths, but the features of the spectrum may differ due to the different resolution and altered appears of scalar coupling. FIG. 1A shows an example of a full NMR spectrum of serum taken under standard conditions on the Vantera® clinical NMR Analyzer by LipoScience, Inc., Raleigh, N.C. The expansion shows that TMAO is in a very crowded region which can confound the quantitation. The normal biological range of TMAO in human serum or plasma is between about 1 to about 50 µM, which may normally be between about 1-10 µM, but dietary spikes can raise the upper value, typically to between about 30-50 µM or even higher. This amount is very low for NMR detection, but this metabolite benefits from the fact that the only signal is a singlet that results from 9 magnetically degenerate protons; thus, the $^1$H signal concentration is 9 times higher than the absolute chemical concentration.

Figure 1B:
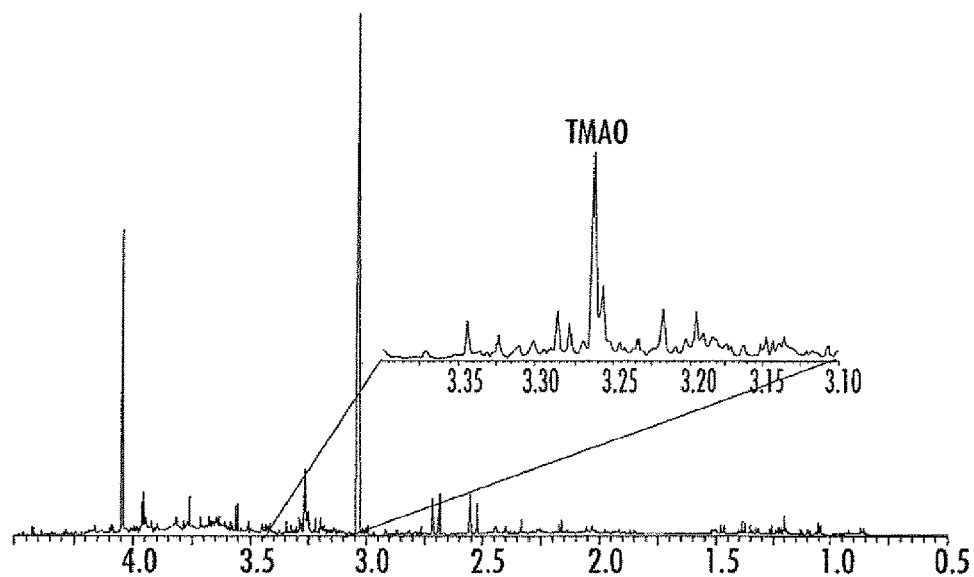
FIG. 1B is an NMR spectrum of human urine with an expansion of the region containing the TMAO peak.

Urinary TMAO is thought to be highly correlated with serum TMAO levels, after correcting for concentration using the creatinine concentration. FIG. 1B shows the NMR spectrum of urine with an expansion around the TMAO signal. TMAO is present in urine at a much higher concentration. In FIG. 1B, the TMAO level is 540 uM, which is more than about 100 times greater than the normal concentrations in serum. Typical urine ranges of TMAO can be between about 0-1000 µM as noted above.

It is contemplated that the normal biological variability may be sufficiently large that only a semi-quantitative test is necessary, e.g., quantitative measures of values associated with a fourth quartile or fifth quintile of a hazard ratio, e.g., the $75^{th}$ percentile or $80^{th}$ percentile, which may be associated with a concentration of about 6.2 µm or greater. In some embodiments, the NMR assay can reliably quantify to at least the $50^{th}$ percentile, e.g., about 3.7 µm or greater for human blood plasma or serum samples. That is, where TMAO is associated with increased risk or abnormal conditions or disease, the amounts of TMAO in a sample can be greater than normal ranges/values and can be more precisely measurable than low levels.

Urinary TMAO levels will likely be more influenced by acute dietary influences whereas the serum assay is likely to more reflective of the chronic TMAO levels. An NMR urinary assay has higher concentrations of TMAO, than is present in serum or plasma, which may allow a similar-high volume throughput. While discussion of diluents, buffers and sample preparation discussed below are applicable to multiple biosample types, particular evaluation protocols for urine biosamples for TMAO will be discussed further below, see, e.g., FIGS. 19, 20A and 20B.

Typically, the NMR analyzer 22 (FIGS. 13A, 14) can diagnostically analyze at least about 400, and more typically at least about 600, samples per twenty-four hours. See, e.g., U.S. Pat. No. 8,013,602 for a description of a suitable NMR analyzer 22 (FIGS. 13A and 14), the contents of which are hereby incorporated by reference as if recited in full herein. FIG. 2A shows an expansion of the serum spectrum shown in FIG. 1A with the pH adjusted. Thus, referring to FIG. 2A, in order to resolve the TMAO peak, marked with an asterisk, from the overlapping metabolites, the pH of the biosample is altered over pH ranges from 2.82 at the top to 7.9 at the bottom. It is clear that there is a significant shift of the peak between pH 4.6 and 5.6. FIG. 2B shows the chemical shift behavior of this TMAO peak over the narrower pH range from 5.15 to 5.53. The region in the NMR spectrum between 3.2 and 3.4 ppm is relatively open, i.e., with fewer significant interferences to TMAO concentration. Thus, in some embodiments, a target pH for the sample can be set to position the NMR TMAO peak between about 3.2 and 3.4, which can be carried out, for example, by adjusting the pH to be between about 5.15 and 5.53. In some particular embodiments, the pH of the sample undergoing analysis can be set to about 5.3 to put the TMAO peak in about the center of the open region.

When analyzing biosamples, such as urine or serum, for example, other peaks may overlap with the TMAO peak but they can be modeled by a peak finding and quantitation algorithm so that accurate measurements can be obtained.

Figure 2C:
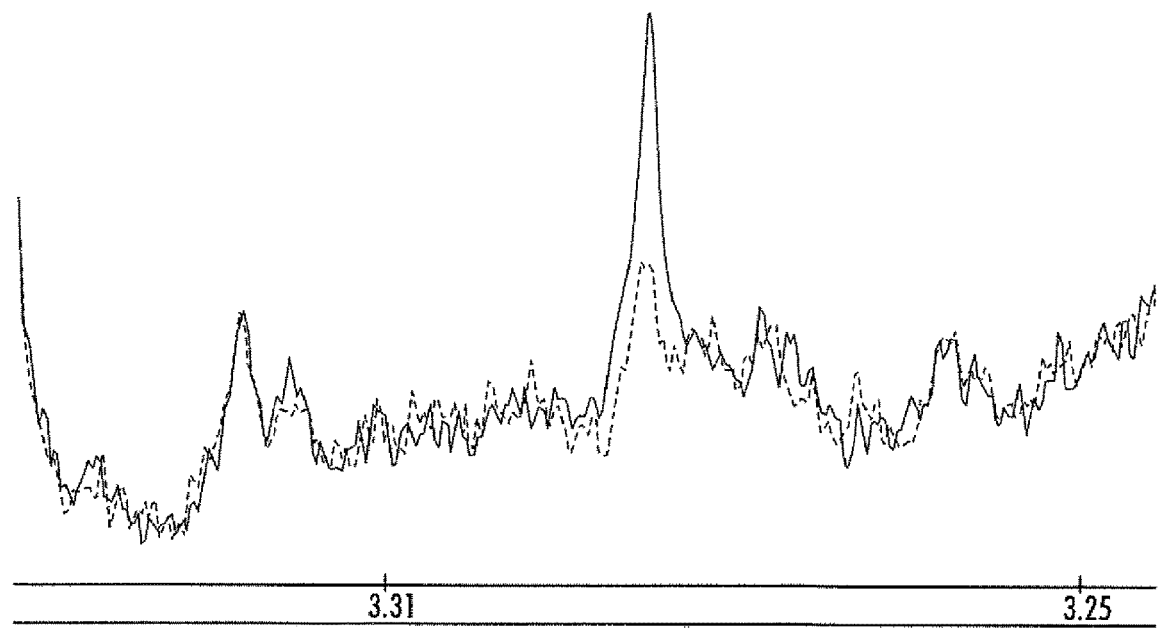
FIG. 2C is an overlay of the TMAO region of NMR spectra collected, one with endogenous TMAO only and one with the addition of a defined amount of TMAO added to the buffer solution according to embodiments of the present invention.

FIG. 2C is an overlay of the TMAO region of two NMR spectra collected, one with endogenous TMAO and one with the addition of a defined (10 uM) amount of TMAO added to the buffer solution. This region displays a number of other background signals which could in some instances confound the quantitation of the TMAO. The addition of a known quantity of TMAO in the buffer solution insures that the TMAO peaks will be the largest peak in this region and therefore can be unequivocally identified. The standard addition also aides in the fitting of the TMAO peak such that the effects of overlapping resonances are minimized in the peak fitting routine. As a known amount of the standard TMAO (e.g., "standard" in a known concentration is used), once the TMAO concentration is measured from the enhanced peak, the concentration added by the TMAO standard diluent is subtracted to yield the TMAO concentration resident in the sample. It is contemplated that a TMAO standard concentration between about 1-100 µM can be used for TMAO biosample evaluations, typically between about 5-20 µM, and more typically about 10 µM.

As will be discussed below, the diluents and/or buffer (including the TMAO standard) can be provided with a defined final concentration to yield a defined blood plasma or serum to buffer ratio, typically of 50:50 or greater, and more typically 75% serum and 25% buffer but more buffer than serum can also be used. However, other final concentration values and ratios may be used as discussed below.

Figure 3A:
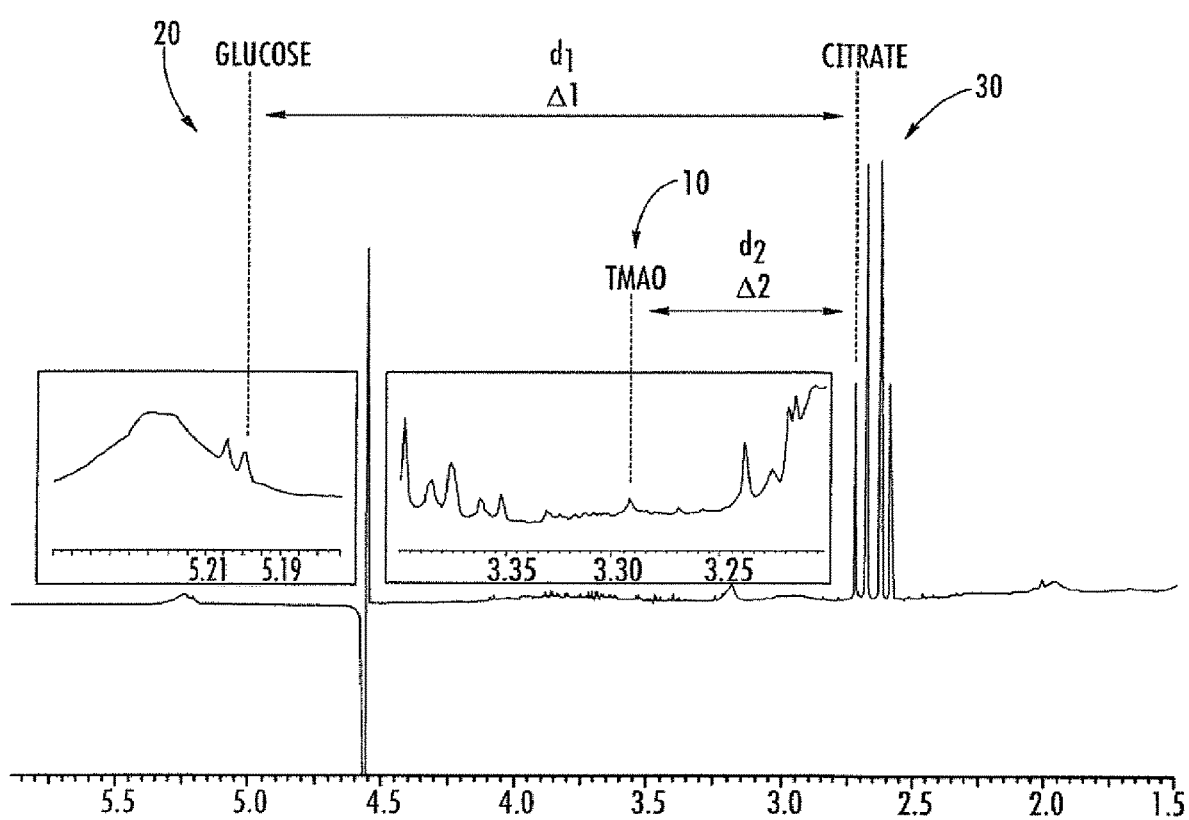
FIG. 3A is a schematic illustration of an NMR spectrum with a reference peak region and a calibration peak region used to determine a location of the TMAO peak according to embodiments of the present invention.

Referring now to FIG. 3A, in some embodiments, to facilitate locating the TMAO peak region 10, recognizing that commercial application may be such that some samples may have slight variations in pH, a pH stable reference peak region 20 in the NMR spectrum of the biosample can be utilized. In some embodiments, the reference peak region is associated with glucose which is in the biosample. This does not require that a reference analyte be added to the sample to create the reference peak 20. However, it is contemplated that other reference peak regions may be used using added reference material or other pH stable constituents in the biosample. For some biosamples, such as urine, other added or natural (internal shift standards) or reference compounds can be used, e.g. TSP (the sodium salt of trimethylsilylpropionic acid (including deuterated version), DSS (4,4-dimethyl-4-silapentane-1-sulfonic acid), and the like can be used as well as other pH stable chemicals and/or compounds.

As shown in FIG. 3A, a defined calibration reference peak region 30 with signal intensity greater than TMAO can also be used. The location of the calibration peak region varies or changes with pH. The distance "d1" between the stable reference peak region 20 and the calibration peak region 30 (one or more of the citrate quartet peaks) can be calculated. Then, based on a defined relationship between the location of the calibration peak region 30 and the relative position of the TMAO peak region 10, the distance "d2" can be determined which identifies the location of the TMAO peak region 10. The calibration peak region can be one or more peaks of a citrate quartet peak region. However, other pH varying calibration peak regions may also be used.

Figure 3B:
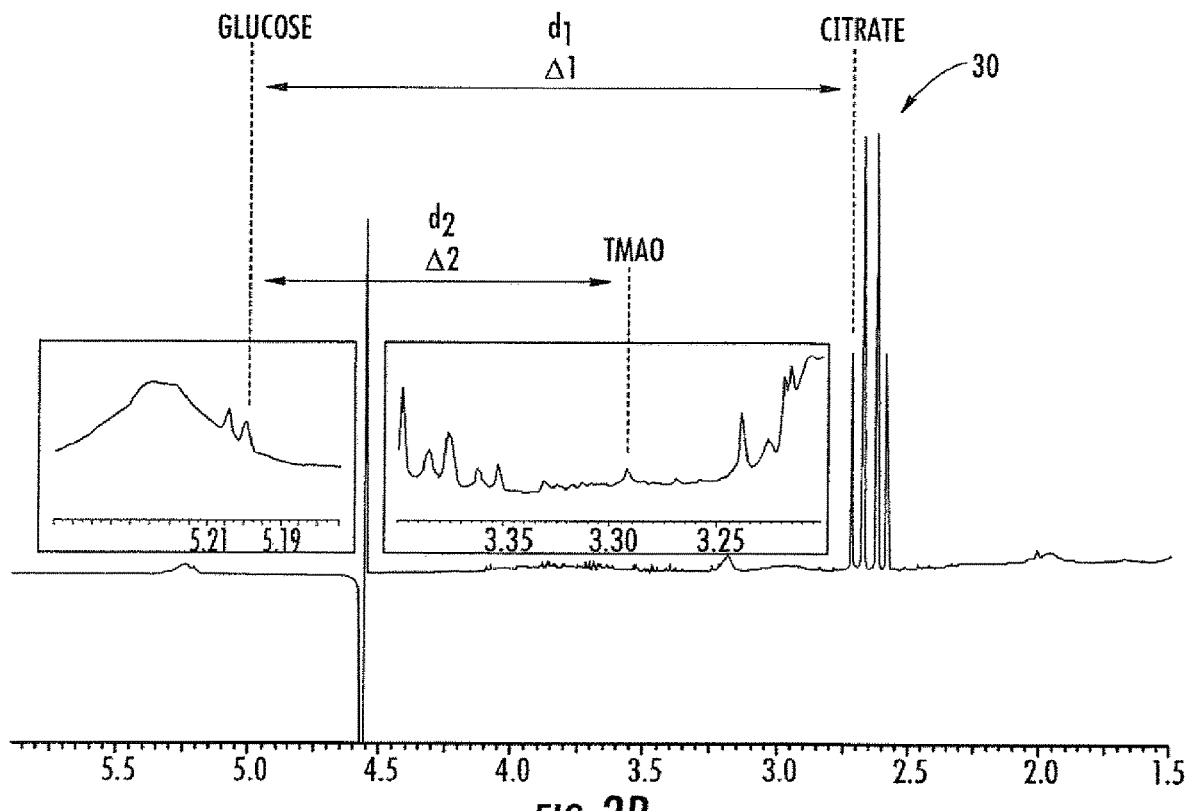
FIG. 3B is a schematic illustration of an NMR spectrum with a reference peak region and a calibration peak region used to determine a location of the TMAO peak according to other embodiments of the present invention.

FIG. 3B illustrates a method similar to that shown in FIG. 3A, but the TMAO peak location can be calculated based on a distance d2 between glucose and TMAO rather than citrate and TMAO.

Figure 3C:
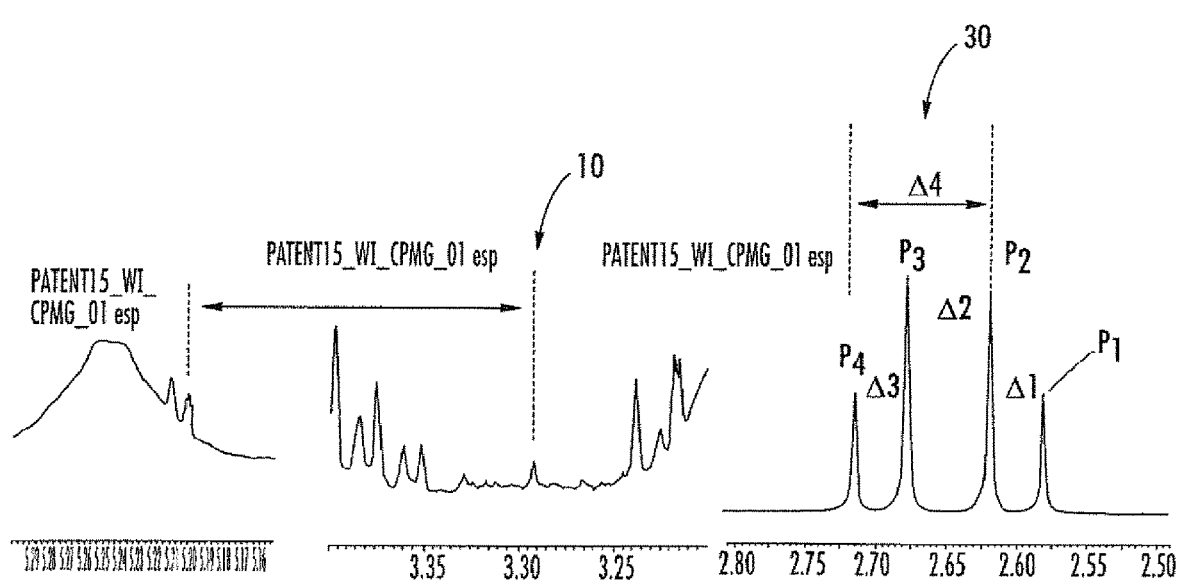
FIG. 3C is a schematic illustration of an NMR spectrum with a pH-variable calibration peak region used to determine pH and/or a location of the TMAO peak according to embodiments of the present invention.

In some embodiments, as shown in FIG. 3C, the location of the TMAO peak region can be determined without the use of the pH-stable reference peak region. As shown, two or more peaks of a pH-variable calibration signal, e.g., the individual peaks of the citrate multiplet 30 can also give pH information, as the distance between these peaks varies as a function of pH. The distance between peaks can be used to determine the TMAO peak location. The distance can be calculated based on leading edges, trailing edges or a center of the peak. This embodiment does not require a separate reference compound/reference peak region 20 as the calibration peak region can be used to define pH that is used to define the TMAO peak location. As shown, there are four peaks associated with the calibration multiplet, shown as P1-P4 (right to left), and a distance "Δ" between each adjacent peak and a distance Δ between other combinations of the peaks, e.g., between any or combinations of P1-P2, P2-P3, P3-P4, P1-P3, P1-P4, P2-P4 and the like including a summative distance between each or combinations of peaks that may be used to identify a pH level. This distance changes as the chemical structure bends in response to pH level of the biosample. Thus, one or more distances between one or more of the peaks in the citrate multiplet can be used to identify pH level, which can then be used to locate the TMAO peak. The location of the TMAO peak 10 can be based on a look-up table or other computational model that correlates spacing distance to pH level and pH level to TMAO peak location, or may be identified by calculating a distance Δ2 between one or more of the citrate peaks and the projected TMAO peak location.

In some embodiments, recognizing that across the pH range from 5.15 to 5.45, the downfield peak of the citrate shifts downfield by about 52 points (14 Hz), the spectra can be acquired with a sufficient digital resolution, such as, for example, about (16384 pt)/(4496.4 Hz)=(3.64 pt/Hz).

Figure 4A:
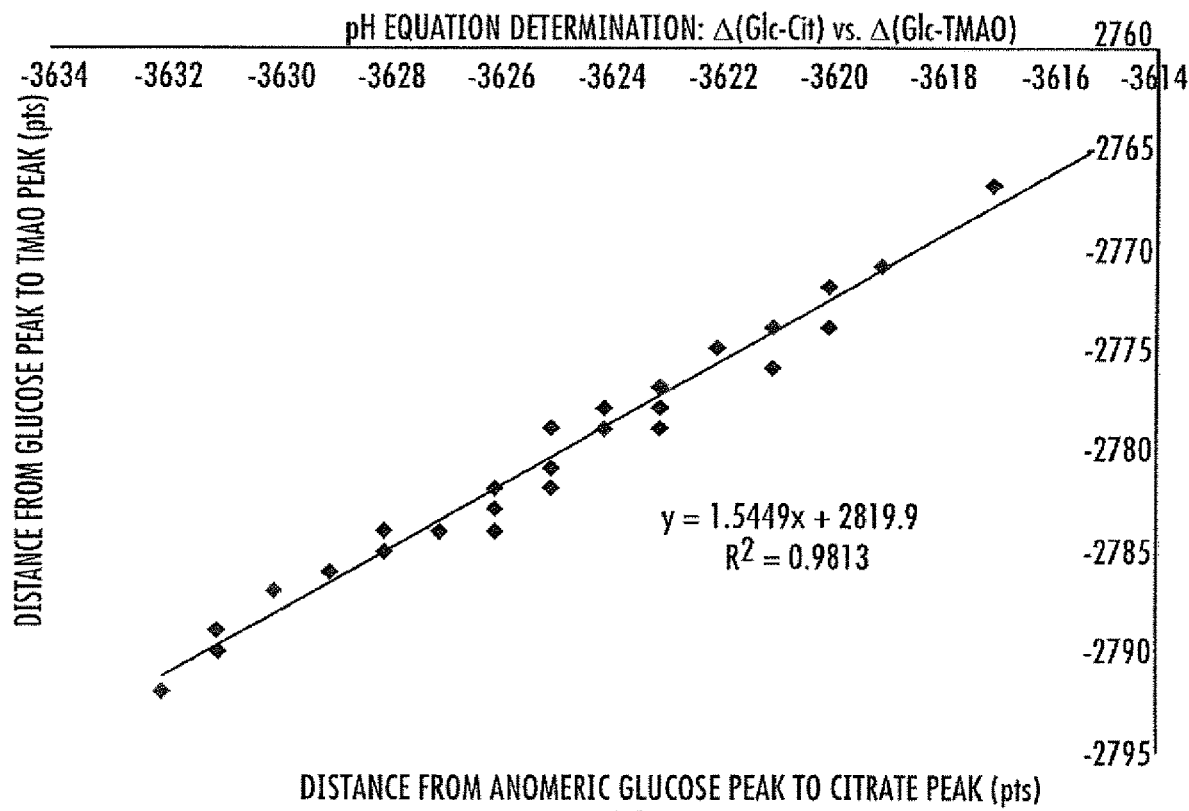
FIG. 4A is a graph of distance between citrate and glucose peak (delta citrate) across the pH range from 5.15 to 5.45. The data shows the defined mathematical relationship between the distance between glucose and TMAO peak (delta TMA) according to embodiments of the present invention.
Figures 4B, 5:
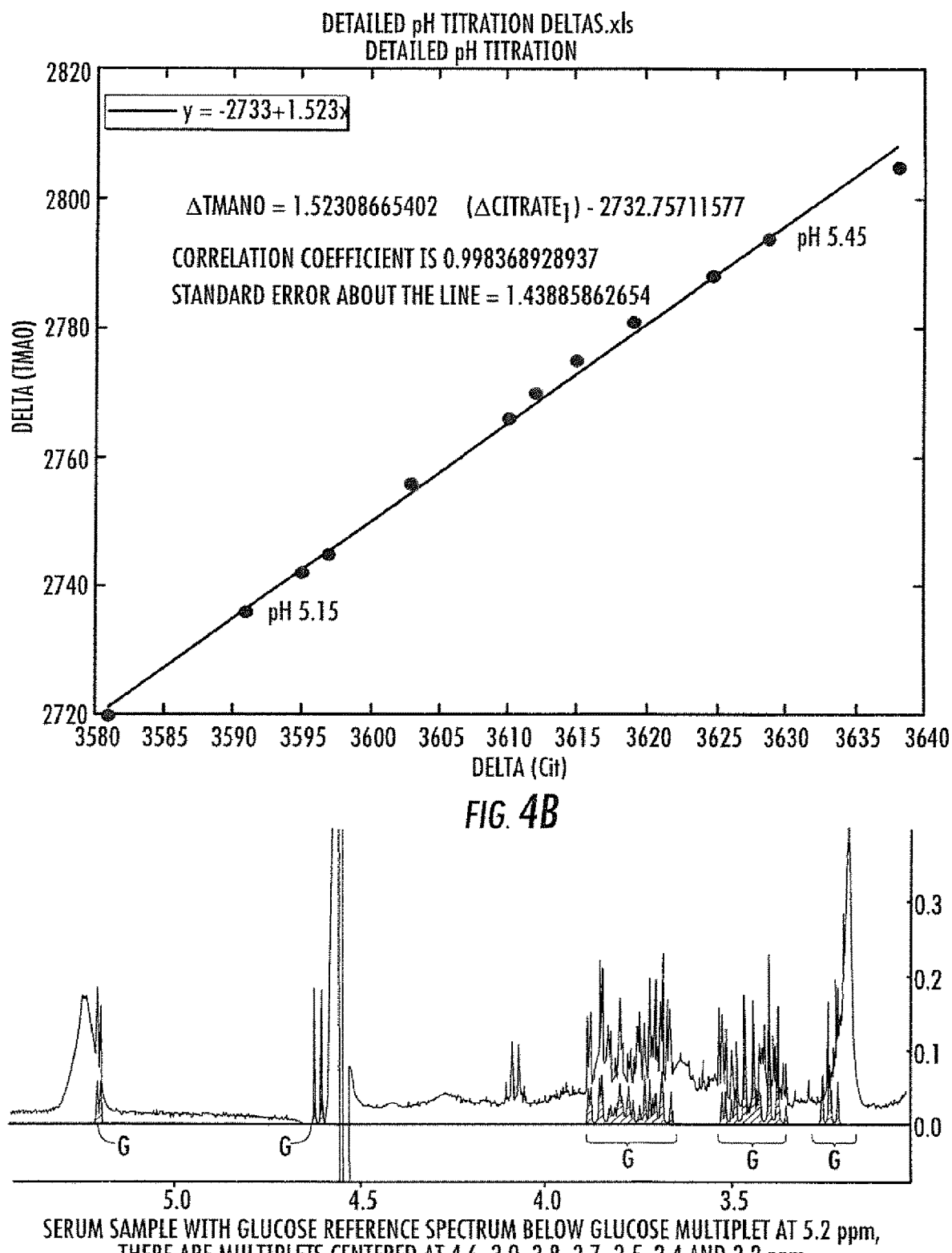
FIG. 4B is a graph of distance between citrate and glucose peak (delta citrate) in a set of patient samples that have a narrow pH range. The data shows the defined mathematical relationship between the distance between glucose and TMAO peak (delta TMA) according to embodiments of the present invention.
FIG. 5 is an NMR spectrum illustrating alternative locations of glucose peak regions according to embodiments of the present invention.

In particular embodiments, the reference peak region can be an anomeric glucose peak region 20 at about 5.20 ppm with glucose peaks that are highly stable to pH and display substantially no shift across this range. The distance between the citrate peak region 30 is linearly correlated to the distance between one or more of the citrate peaks and the TMAO peak. This relationship is shown in FIGS. 4A and 4B. The TMAO peak 10 can be accurately located based on the location of the citrate peak(s) or the glucose peak(s). The locations of the three peak regions 10, 20, 30 and the defined mathematical relationship is believed to be independent of temperature of the sample during analysis and spectrometer field strength.

$$Y = 1.5449x + 2819.9 \quad \text{EQUATION (1A)}$$

where Y is the distance of the TMAO peak from glucose, and x is the distance between the calibration (citrate) peak and the reference (glucose) peak.

$$Y = 1.4924x + 2626 \quad \text{EQUATION (1B)}$$

In summary, a set of samples around the expected range can be prepared. The spectra can be analyzed and the distance between the invariant glucose and the pH sensitive citrate can be measured. The distance from the invariant glucose and TMAO can be measured and a defined mathematical relationship between the two can be determined. Equations 1A and 1B are examples of equations for determining TMAO peak location using glucose. However, it is noted that experimental conditions (pH buffers, NMR spectrometers and the like) can vary and the TMAO peak distance can be calculated from one or more citrate peaks rather than glucose. Thus, these Equations are by way of example only and any similar equation that results in an $R^2$ of ≥0.9 will be considered equivalent to these defined mathematical relationships.

While the glucose peak region 20 (multiplets that are centered) at 5.20 ppm was used in this example, other reference peak or peak regions may be used. In some embodiments, one or more other glucose peak regions may be used such as one or more peaks of glucose multiplets "G" centered at one or more of about 4.6, 3.9, 3.8, 3.7, 3.5, 3.4 and 3.2 ppm as shown by the lower darker lines in FIG. 5.

As noted above, in some embodiments, the location of the TMAO peak region 10 can be determined using one or more of the citrate peaks as the calibration reference peak/peak region. In some embodiments, one peak of the citrate multiplet is found at 3.7 ppm. Given that the typical biosample with the added pH buffer contains a large concentration of citrate (e.g., typically the buffer is at least about 25% by volume), these citrate peaks are easy to find electronically as they are among the largest peaks in the spectrum. The distance between the anomeric glucose peaks 20 and the citrate peaks 30 is related to the distance between the citrate 30 and TMAO peaks 10. This defined mathematical relationship has been shown to robustly determine the location of the TMAO peak within approximately 10 data points.

Given the low signal to noise of the TMAO at the low concentration, finding the actual TMAO peak can be challenging. In some embodiments, the TMAO peak 10 can be determined to be the $1^{st}$ peak maximum that is found near the starting location determined by the calibration peak evaluation. However, it is contemplated that other protocols or algorithms can be used to effectively and efficiently determine the location of the TMAO peak, especially with low TMAO concentrations where the noise and low concentration interferences are more confounding. For example, when the signal to noise is quite low, the peaks 10 may not be readily distinguishable from the noise. In some embodiments, as described above, TMAO can be added to a buffer to "amplify" the signal and/or insure that TMAO will be the largest peak in the region of interest.

In some embodiments, the electronic determination of the expected TMAO peak location can be carried out using a defined linear relationship between the location of the reference peak, the location of the pH sensitive calibration peak, and the location of the TMAO peak. The (probable) actual TMAO peak location can be identified by weighting the region around the expected TMAO peak location with a Gaussian or similar function such as, but not limited to, triangular and parabolic functions.

Figure 3D:
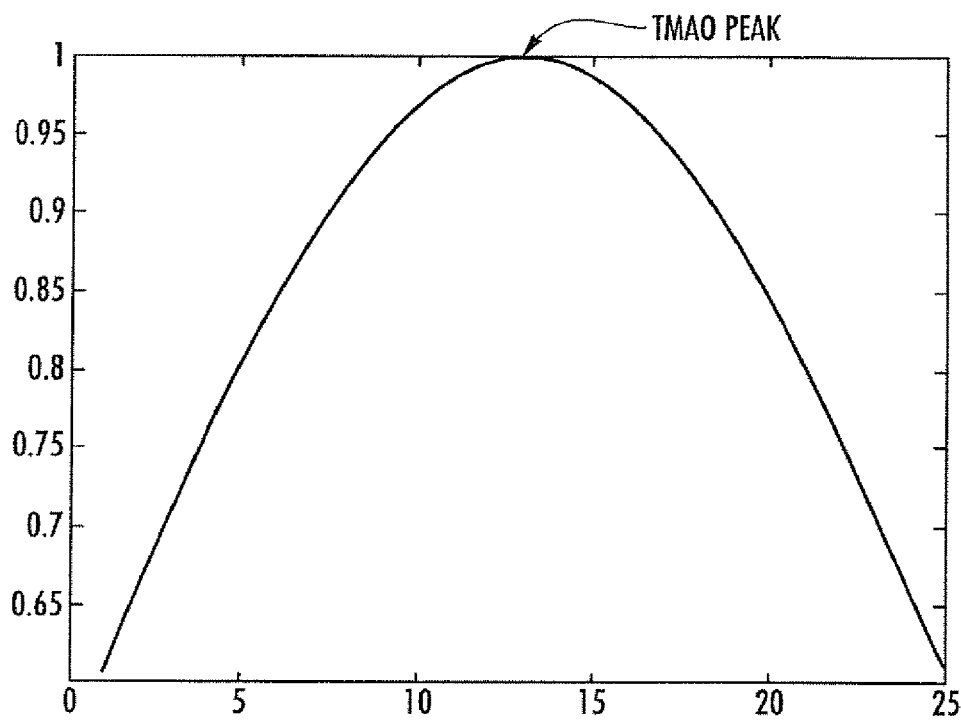
FIG. 3D is a graph of a weighted function that can be used to identify a probable actual TMAO peak location according to some embodiments of the present invention.

The probable actual TMAO peak location can then identified as the highest weighted data point. The algorithm can mathematically emphasize the search for the actual peak around that location. FIG. 3D shows an example function in which the highest point on the curve corresponds to the probable actual TMAO peak location. The search for the actual TMAO peak will therefore be weighted toward that location. Thus, the highest weighted data point of the weighted region is defined as the probable actual TMAO peak location which can be used as the center point of the fitting region to determine the level of TMAO.

The fitting region can include between about 30 to about 50 data points centered about the calculated (probable) actual location of the TMAO peak. The fitting region can be electronically curve fit with a defined curve fitting function or functions. The curve fit can selectively allow for one or more neighbors on either side to account for small misalignments to determine the level of TMAO.

Figure 6A:
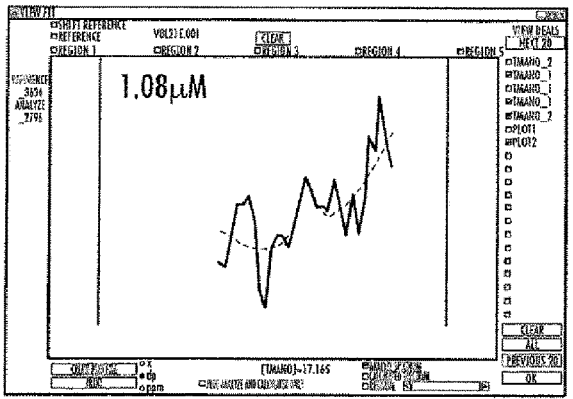
FIGS. 6A-6F are graphs of curve fitting for different amounts of TMAO in a sample according to embodiments of the present invention.
Figure 6B:
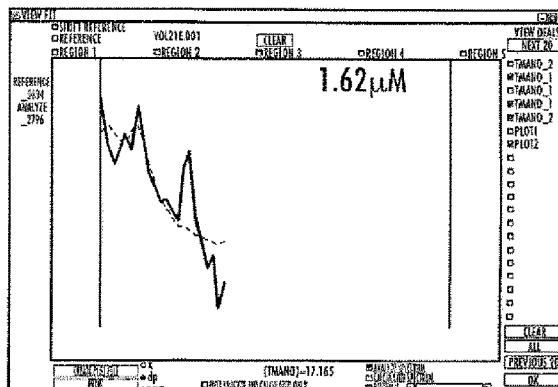
Figure 6C:
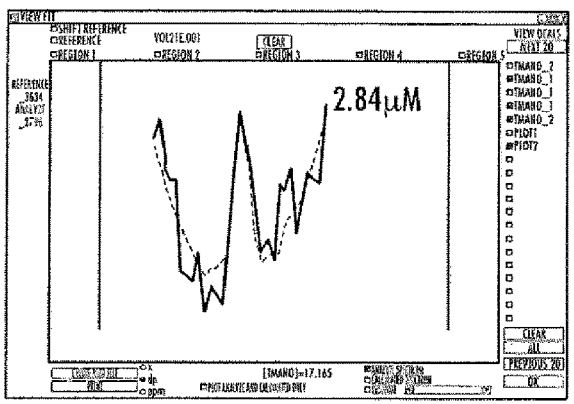
Figure 6D:
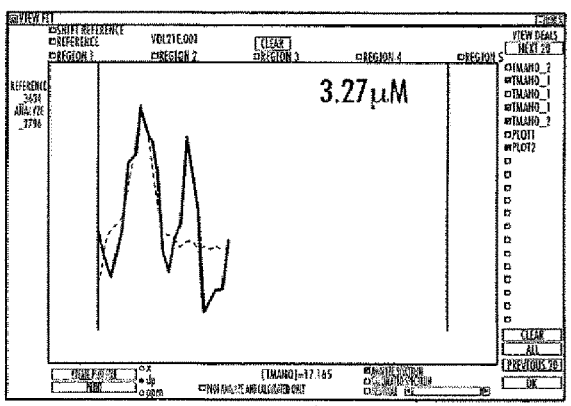
Figure 6E:
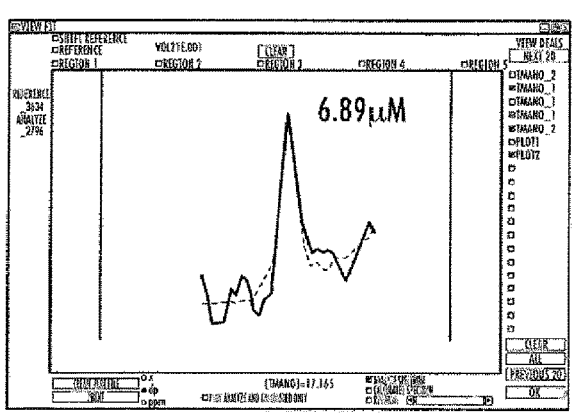
Figure 6F:
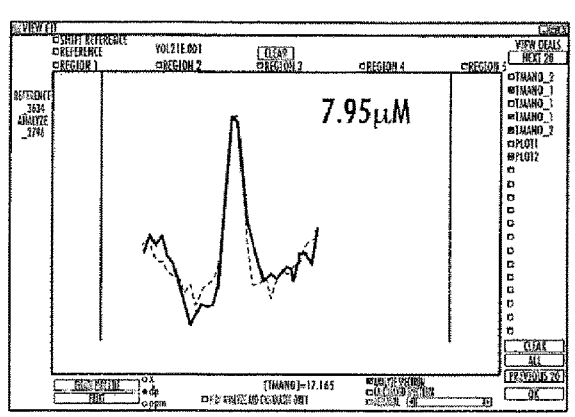

FIGS. 6A-6F illustrate curve fitting of TMAO peaks from patient biosamples with concentrations in the $1^{st}$ (6A, 6B), $2^{nd}$ (6C, 6D) and $4^{th}$ (6E, 6F) quartiles. The quartile ranges are by way of example only and are estimates from literature values. See, e.g., Wang et al., Gut flora metabolism of phosphatidylcholine promotes cardiovascular disease, 58 Nature, Vol. 472, Apr. 7, 2011, the contents of which are hereby incorporated by reference as if recited in full herein. These values may change with additional evaluation of clinical data or over time. The TMAO peaks can have a narrow width of less than 2 Hz, more typically about 1.5 Hz or less, e.g., about 1.2 Hz to about 0.6 Hz, and the peak shape can vary and may have an asymmetric shape, e.g., a non-Lorentzian shape. In order to account for small differences in the linewidth of the TMAO peak, a curve fitting technique can be used. The line shape and linewidth can vary which can make quantitation difficult. The fits in FIGS. 6A and 6B are not ideal and quantitative measures of TMAO at this low end may be unreliable. However, the fits in FIGS. 6A and 6B yield low values that would accurately categorize the patient as being in the 1st quartile or quintile, for example.

It is contemplated that patients having high TMAO values (in the $4^{th}$ quartile or $5^{th}$ quintile, for example) relative to a defined population are considered to be "at-risk" or as having an elevated risk relative to the population norm.

In order to account for small differences in the linewidth of the TMAO peak, a curve fitting technique can be used. The curve fitting may use different sets of basis functions that can vary biosample to biosample, which can include none, or one or more neighboring TMAO peaks that reside on adjacent the main TMAO peak.

Figure 7A:
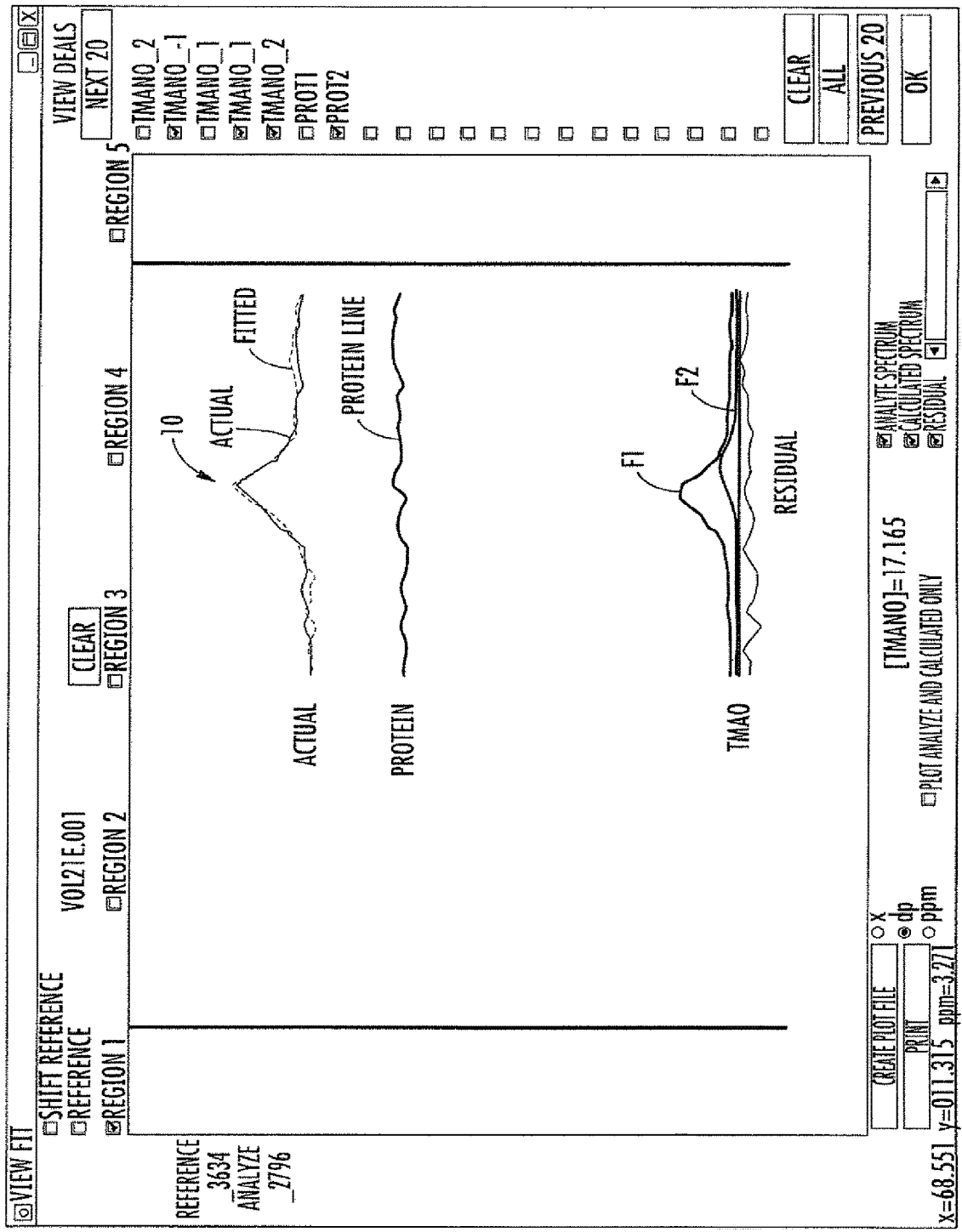
FIG. 7A is a graph showing curve fitting of the actual TMAO peak with multiple TMAO and protein basis functions according to embodiments of the present invention.

Once the TMAO peak 10 has been found, it can be computationally fit using one or more defined fitting functions as shown in FIG. 7A. The two composite lines shown at the upper portion represent an actual line, marked "actual" and a fitted line, marked "fitted" and shown in broken line. As shown on the bottom of FIG. 7A, the TMAO fitting functions can include a primary function F1 and at least one secondary function F2 which may be programmatically used selectively if the curve fitting is not sufficiently accurate for a particular biosample. The basis functions can be pre-defined and selected for use programmatically based on certain defined measurement or curve fitting decisions and can be configured to include none (only the primary basis function F1), or one or more of different pre-defined secondary curve fitting or secondary basis functions which may use one, two or three neighboring peaks of the TMAO peak.

The analysis circuit or module (e.g., at least one digital signal processor) can be programmed or otherwise configured to decide whether one or more secondary curve fitting functions is appropriate for any particular biosample. Thus, the analysis may vary biosample to biosample based on a defined set of alternate curve fitting functions. The one or more secondary curve fitting functions F2 may use one or more neighboring TMAO peaks to help more accurately or reliably fit this region.

The fitting can include a set of basis functions that include a TMAO peak (e.g., the primary function F1 and optionally one or more secondary functions F2) as well as a quadratic function that accounts for the residual protein baseline interferences (bottom of FIG. 7A) that survive the pulse sequence. The TMAO basis function can be an experimentally acquired spectrum of TMAO processed with consistent parameters to the actual spectrum. Computationally derived TMAO basis functions, i.e., specified functions comprised of Lorentzians, Gaussians or some combination of both can also be used.

The lineshape deconvolution can be achieved with a non-negative least squares fitting program (Lawson, C L, Hanson R J, Solving Least Squares Problems, Englewood Cliffs, N.J., Prentice-Hall, 1974). This is avoids the use of negative concentrations which will lead to error due especially in low signal to noise spectra. Mathematically, the lineshape analysis was described in detail for lipoproteins in the paper by Otvos, J D, Jeyarajah, E J and Bennett, D W, Clin Chem, 37, 377, 1991. Referring particularly to the equation in the left column of page 379. In this equation, Vji can represent the TMAO peaks (including main peak and optionally one or more neighbors) and Vki can be the protein components. A synthetic baseline correction function may also be used to account for baseline offsets from residual protein components. This can take the form of a quadratic or other polynomial function. Weighting factors are determined and the fit can be optimized by minimizing the root mean squared deviation between the experimental and calculated spectrum. See also, U.S. Pat. No. 7,243,030, the contents of this patent and the Otvos et al. article are hereby incorporated by reference as if recited in full herein.

The relative TMAO concentrations determined have no physical meaning. A linear calibration function can be determined which relates the integral units from the spectrometer to micromolar concentration values. The calibration function is determined by measuring the signals of samples with known concentrations of TMAO. These are typically samples prepared by spiking TMAO into extensively dialyzed plasma which has all of the small molecule metabolites dialyzed away.

Figure 7B:
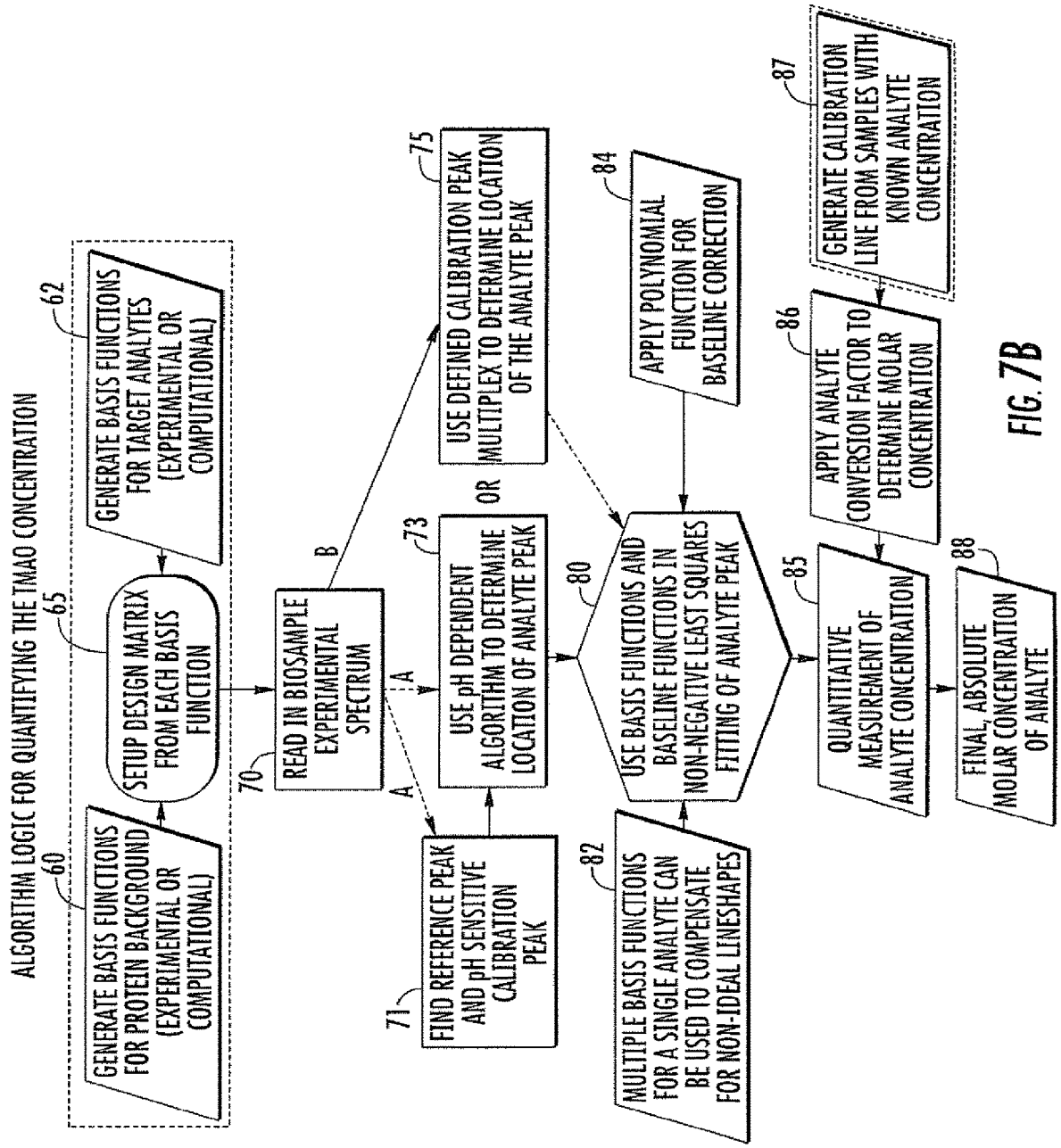
FIG. 7B is a flow chart of an intelligent TMAO curve fitting function according to embodiments of the present invention.

FIG. 7B is a flow chart that illustrates exemplary operations or steps that can be used for selecting basis functions for the TMAO curve fitting analysis. The boxes shown with a broken line perimeter indicates that these operations or steps can be generated prior to analysis of respective biosamples. As shown, the basis functions for the protein background and target analytes are defined (block 60, 62) and the design matrix from each basis function is also defined (block 65). A biosample spectrum is obtained (electronically read or otherwise provided or obtained) (block 70). The location of the analyte (e.g., TMAO) peak is determined using either blocks 71, 73 (the reference peak and calibration peaks are determined, then a pH dependent relationship is used to determine the location of the analyte peak), or a calibration multiplet is used with distance between peaks varying according to pH (block 75). The basis functions and baseline functions are used in non-negative least squares fitting of the analyte peak region (block 80) which can selectively include the use of one or more of several defined basis functions for a single analyte to compensate for non-ideal lineshapes that maybe present in a particular biosample (block 82). A polynomial function can be applied for a baseline correction (block 84). An analyte conversion factor can be applied to determine a molar concentration of the biosample (block 86). This conversion factor can be based on a calibration correlation defied using known analyte samples of different concentrations (block 87). The final concentration of the analyte can be output, such as to a patient report (block 88).

It is technically challenging to fit peaks in experimental spectra from complex mixtures such as biofluids, where signals from other components of the sample can interfere with the signal of interest and peaks can have non-ideal lineshapes. Factors including, but not limited to, differential protein binding, ionic composition and field inhomogenity can lead to non-Lorentzian, sometimes asymmetric peak shapes. To fit these types of peaks, embodiments of the invention provide the option to use additional analyte basis functions that are placed on either side of the main peak. Where used, the neighbors can be placed in one point increments on either side of the main peak, with up to 3 neighbors on each side. The number of neighbors allowed in a fitting protocol can be set prior to the analysis and is dependent upon the spectral characteristics of the assay including signal to noise ratio and potentially confounding signals. The contribution of the main peak plus the neighbors as well as the protein basis functions and baseline correction function can be evaluated using the non-negative linear least squares algorithm (block 80). Thus, deconvolution of the small, single, pH-dependent TMAO peak typically takes place after determining its exact (or substantially exact) location based on a defined mathematical relationship between the pH-dependent reference and TMAO.

In order to deconvolute the TMAO peak located upfield from the water peak, a sixty data point search window can be established from predetermined parameters in the program setup menu. The search window covers all the possible TMAO locations across all (normal) patient samples. The analysis can use a pH-independent reference present in patient samples, such as the anomeric glucose peaks, to determine the location of this 60 data point window in the spectrum. The approximate location of the glucose doublet (located downfield of the water peak) is specified within the program and a least squares fit is performed to find an exact match between the doublet and a Lorentzian lineshape. However, as noted above, a calibration reference multiplet can alternatively or also be used.

Because the TMAO peak (located upfield from the water peak) often has a very small amplitude, it is difficult to locate its position accurately, especially in the presence of other analytes with similar concentrations. However, it is possible to determine the exact location of the TMAO peak relative to a citrate reference peak located upfield from the TMAO resonance, since there is a defined mathematical relationship relating the location of the pH dependent downfield citrate resonance and the separation of the citrate and TMAO peaks. The analysis locates the position of one or more of the citrate peaks, again using a least squares fit with a Lorentzian lineshape. This location can be entered into an empirically determined function that calculates the position of the TMAO peak.

After locating the position of the TMAO peak, the size of the fitting region can be reduced, typically to about 30-50 data points, centered around the calculated location of the TMAO peak. The size reduction from the larger search window to the smaller fitting window can diminish potential interferences from other metabolites. Finally, the analysis model can employ a single real TMAO basis component to deconvolute the peak while also allowing for one neighbor on either side to account for small misalignments. In addition, the minimal protein baseline present in the TMAO fitting region can be modeled with three quadratic equations: positive, negative and zero (a line). The least squares fit can be performed with a 30 data point analyte vector (the spectrum in the 30 point window) and a 30×6 design matrix, consisting of three TMAO basis vectors (the TMAO basis component and its neighbors—shifted by a single data point to each side) and the three baseline correction vectors. The fitting coefficients are generated from a Lawson-Hansen non-negative least squares QR fit (on just the thirty data point fitting region), resulting in coefficients that are then multiplied by concentration factors and combined to generate the final TMAO concentration.

FIGS. 3 and 4 illustrate one embodiment that can find the location of the TMAO peak by calculating the distance between glucose and citrate versus the distance between glucose and TMAO. In other embodiments, the TMAO location can be based on the distance between citrate and TMAO. In the embodiment discussed with respect to FIGS. 3 and 4, for example, the following protocol can be used.

1. Find the pH stable glucose
2. Determine distance to citrate
3. Plug distance into defined linear equation (e.g., Equation 1A, 1B) as "x"
4. Calculate distance from glucose to TMAO As noted above, a predefined established relationship for the $\Delta$ between glucose and citrate vs. the $\Delta$ between glucose and TMAO can be used to calculate TMAO location. For example, as shown in FIGS. 3, 4, the citrate position relative to glucose can be determined by subtracting the position of citrate from that of glucose per Equation 2.

a. $7272 - 10908 = -3636$      Equation 2 b. The 'citrate position' can be inserted into the defined linear equation (along the lines of Equation 1A or 1B), e.g.: $y=1.4924(-3636)+2626$. This value, $y=-2800$ defines the TMAO distance from glucose.

c. The actual TMAO position can then be calculated.

$7272 - x = -2800$      Equation 3

Thus, in this example, $x=10072$, which is the TMAO position (peak center).

The temperature for this assay can be any appropriate temperature, typically between about 20 degrees C. to about 47 degrees C. However, measurement of TMAO does not require an elevated temperature. Some preliminary examinations have indicated a very slight increase in sensitivity when the NMR assay is run at 25 degrees C. This small improvement is not likely to have a significant impact in overall assay performance. If this assay were to be run at a different temperature, then all TMAO assays can be run at one time i.e., in batches, to avoid any potential need for frequent and time consuming temperature changing and equilibration when performing tests at other temperatures.

The pulse sequence parameters can include any appropriate parameters including solvent suppression scheme, pulse angle and acquisition time. However, generally stated, in some particular embodiments, the NMR signal acquisition time per scan, for any one biosample, can be between about 2-4 seconds (on average) and typically between about 3-4 seconds (on average), such as about 3.07 seconds (on average). The NMR analyzer may be configured to obtain at least 16 scans per biosample, typically between 16-256 scans, such as ≥64 scans, and more typically ≥96, such as 96 scans or 128 scans with at least about 16K data points collected over a 4400 Hz sweep width, per sample, to obtain the NMR data used to measure TMAO.

One element in the pulse sequence is the solvent suppression scheme. A WET solvent suppression scheme uses a series of shaped pulses and pulsed field gradients over the course of 80 ms. The 1D NOESY-presat scheme uses the first increment of a 2D Nuclear Overhauser Effect Spectroscopy (NOESY) experiment (Beckonert, O.; Keun, H. C.; Ebbels, T. M. et. al. *Nat. Protoc.* 2007, 2, 2692-2703). In this scheme, a continuous low power, frequency selective pulse on water resonance is applied during D1 and 'mixing' time. The PURGE solvent suppression scheme (Simpson, A. J.; Brown, S. A. *J. Magn. Reson.* 2005, 175, 340-346) uses a continuous low power, frequency selective pulse on water resonance, relaxation gradients and echoes to attenuate the water signal.

The performance of all three sequences (and potentially other sequences known to those of skill in the art) is sufficient to achieve consistent spectra. One advantage of the WET sequence is that it does not involve any low power saturation period which could perturb the protein baseline via spin diffusion. It also does not have any significant delays which could lead to signal attenuation via relaxation.

As is well known, a standard presaturation ("Presat") pulse sequence can be used to obtain the NMR spectrum for analyzing the TMAO signal. This pulse sequence involves a selective low power pulse targeting the water resonance and lasting several seconds. This is well established in NMR practice and is a robust and reliable method to attenuate the water signal.

In some embodiments, the WET water suppression scheme can be used. The WET sequence involves a series of short selective pulses targeting the water resonance. The entire scheme is prefixed to the pulse sequence as is the Presat, but only requires 80 ms. The other advantage of the WET sequence is the fact that this sequence imposes only a minimal perturbation on the protein signals. Due to the length of a typical Presat sequence, some of the solvent saturation can be transferred to the protein which can lead to inconsistent contributions of the protein to the baseline. Other solvent presaturation schemes can be used, e.g., a PURGE sequence.

Figure 8:
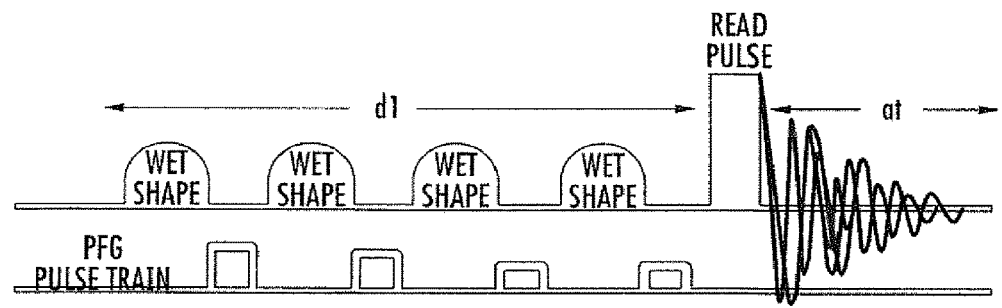
FIG. 8 is an exemplary pulse sequence using a standard "one-pulse" protocol with WET solvent suppression according to embodiments of the present invention.
Figure 10A:
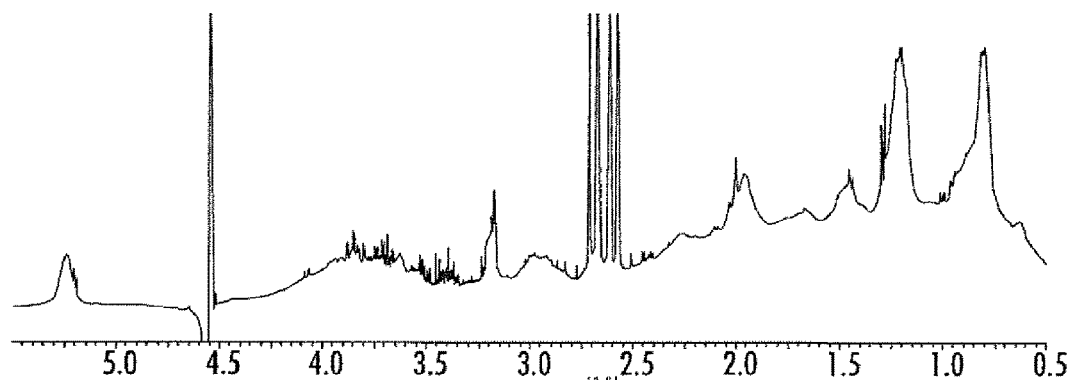
FIGS. 10A and 10B are NMR spectra acquired using the pulse sequence of FIG. 8 (FIG. 10A) and that of FIG. 9 (FIG. 10B). The broad signals from macromolecules are reduced in the CPMG pulse sequence according to embodiments of the present invention.
Figure 10B:
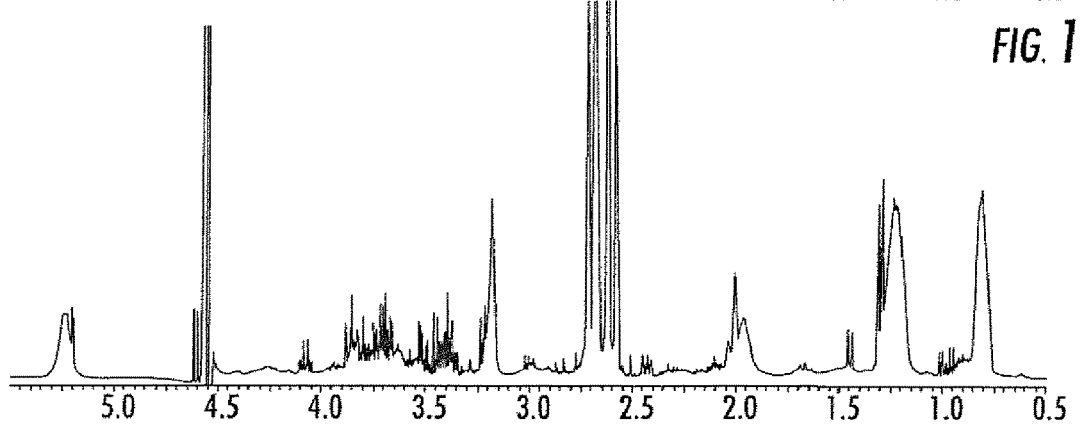

FIG. 8 illustrates a standard "one-pulse" sequence with WET solvent suppression. This leads to a spectrum in which the signals from the high concentrations of proteins and macromolecular aggregates, e.g. lipoprotein particles, dominate the spectra (FIG. 10, upper profile line). The lower concentration, small molecule metabolites are greatly obscured in these spectra. As shown in FIG. 8, the WET solvent suppression scheme (Smallcombe, S. H.; Patt, S. L.; Keifer, P. A. *J. Magn. Reson., Ser. A* 1995, 117, 295-303) includes a series of solvent-directed selective pulses and pulsed field gradients followed by a read pulse and an acquisition time during which the signal is digitized for a fixed amount of time.

Figure 9:
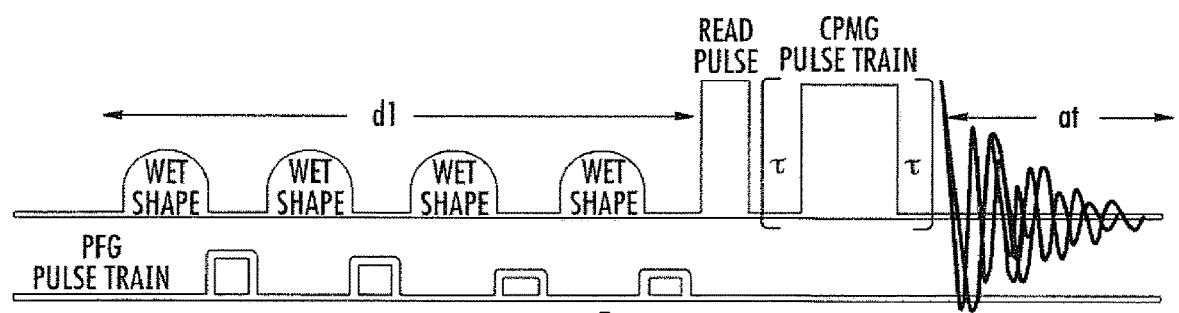
FIG. 9 illustrates the first pulse sequence in FIG. 8 modified to include a CPMG sequence to attenuate signals associated with macromolecules and large aggregates such as proteins and lipoproteins s according to particular embodiments of the present invention.

The second sequence shown in FIG. 9 incorporates a CPMG pulse train or sequence. This pulse train includes a series of refocusing $\pi$ pulses (180 degrees) during which the signals from large, rapidly relaxing molecules are attenuated. The duration of this pulse train can be optimized to minimize the background signals from macromolecules, e.g. proteins and lipoprotein particles, while maintaining most of the signal intensity from the small molecules such as TMANO. This value is set to 100 ms. Thus, the CPMG pulse train shown in FIG. 9 (for CPMG spectrum in FIG. 10B, upper profile line) is designed to attenuate the signals from the macromolecules which facilitate the detection of many more small molecule metabolites. This pulse sequence relies on the fact that the signals from macromolecules relax much faster than small molecules. The spin-echo train occurring can occur after the read pulse and is designed to maintain the small molecule magnetization while the signals from the macromolecules relax back to equilibrium. The duration of this spin echo train relates to the degree of attenuation of the macromolecule signals. This delay is typically set to around 100 ms. It is expected that there will be little perceptible change in performance over the range from approximately 60 ms to 150 ms. However, below 60 ms the protein attenuation may be compromised and above 150 ms the overall signal intensity loss from relaxation may be unsatisfactory.

Comparisons of signal to noise and assay performance were marginally better with the CPMG over the WET. However, it is contemplated that the use of a CPMG sequence can allow the detection of many more metabolites should the assay composition expand in the future. CPMG sequences are well known to those of skill in the art.

In order to obtain an increased (e.g., maximum) signal from a molecule, a 90 degree pulse can be used and the time between these pulses should be in excess of 10 times the longitudinal relaxation time (T1) of the signal. The T1 for TMAO in dialyzed plasma was determined to be about 2.4 seconds. This is not a time efficient means to maximize the signal intensity so a compromise between pulse length and inter-pulse delay can be made. The relationship between signal intensity, T1, and pulse length is given by the Ernst angle equation. The first step in using this equation is to define the length of the entire pulse sequence. The length is defined by the required solvent suppression period, the CPMG delay and the length of the data acquisition period needed to provide the required digitization of the FID. The Ernst angle equation is as follows:

$$\text{Cos (theta)} = \exp -(\text{total delay})/T1 \qquad \text{EQUATION (4)}$$

In equation (4), the total delay equals the d1 delay (including solvent suppression), the CPMG time, plus the acquisition time. T1 represents the longitudinal relaxation time of the analyte signal of interest. It is noted that in front of the parentheses containing "total delay" is a negative sign. Solving for theta will give an optimal flip angle.

Current results indicate that the optimal pulse flip angle for TMAO is about 70 degrees. The equation is relatively insensitive in this region so it is unlikely that small errors in calibration or small differences in the T1 due to specific sample composition will lead to significant inefficiency.

As noted above, the acquisition time (AT) is the time that the FID is digitized. The duration of AT is determined by both the relaxation time of the signal(s) being quantified and the required digitization. If the relaxation time of the signal being examined is longer than the AT then the FID will become truncated resulting in a signal with poor shape. As mentioned above, the T1 relaxation time for TMAO is about 2.4 seconds in serum and thus the acquisition time should be at least that long. The digitization rate of the spectrometer, i.e. the number of points taken per second of acquisition time, is determined by the sweep width of the spectrum. In some embodiments, a desired digital resolution uses at least 16K data points that are collected over the 4400 Hz sweep width. This can employ between about 2-4 seconds, typically about 3.07 seconds, of AT per scan and a plurality of scans can be used per biosample such as between 16-384 scans, typically ≥16 scans, more typically ≥64 scans, such as ≥about 96 scans, such as 96 scans, 128 scans, and 192 scans.

The most direct way to increase the detection sensitivity is to increase the number of scans. In some embodiments, the TMAO assay can be carried out on samples at about 47 degrees C. so that this assay can be easily interleaved with the current LipoProfile® assay. However, as the number of scans increases, the residence time of the sample in the probe at 47 degrees increases and the samples may become denatured. The challenge is to achieve the requisite signal-to-noise ratio for the TMAO peak to allow accurate and precise quantification over a desired biological range (at least those with adverse clinical association).

Figure 11:
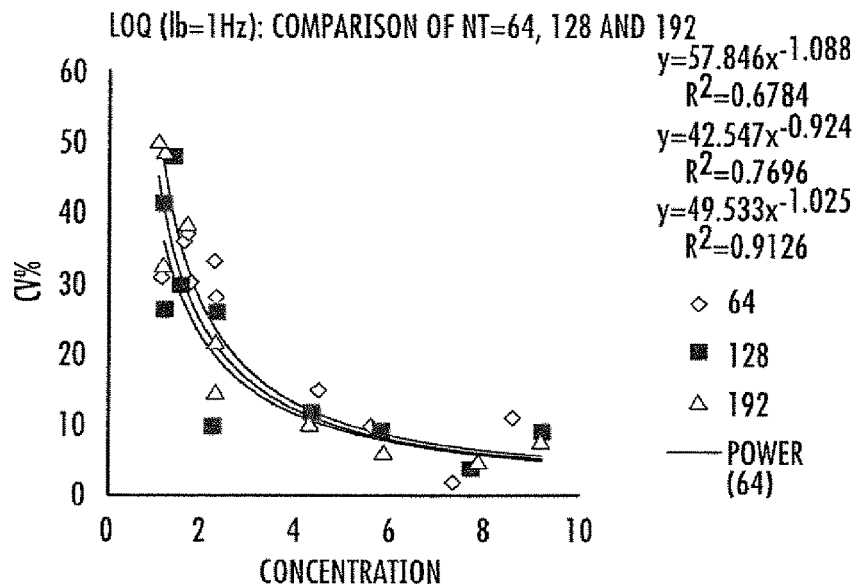
FIG. 11 is a graph of concentration versus CV % for LOQ for 64, 128 and 192 scans according to embodiments of the present invention.

The data can optionally be collected in blocks of 8 so the assay performance can be evaluated considering scans in multiples of 8. FIG. 11 shows the assay performance using spiked dialyzed serum with 64, 128 and 192 scans. Dialyzed serum is an "ideal" matrix in that there are no confounding small molecule metabolites.

Figure 12A:
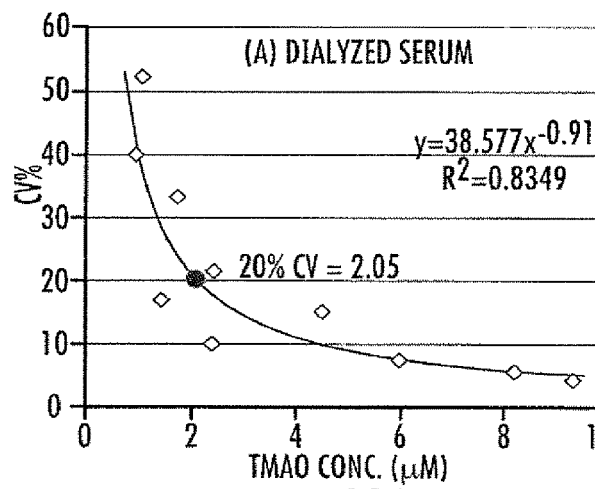
FIG. 12A is a graph of % CV versus TMAO concentration (μM) from spiked dialyzed serum according to embodiments of the present invention.
Figure 12B:
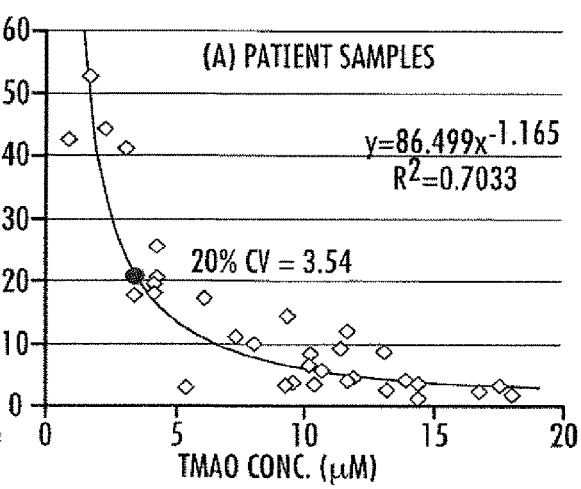
FIG. 12B is a graph of % CV versus TMAO concentration (μM) from patient blood serum samples according to embodiments of the present invention.

The current data shown in FIGS. 12A and 12B indicate that with 96 scans the LoQ is near 2.0 µM. The LoQ for actual patient samples is near 3.5 µM. The medical decision limit, indicated in the Nature paper by Hazen (incorporated by reference above), is approximately 6.1 µM. The performance with 96 scans is sufficient to achieve a quantitative assay that can quantify TMAO in the clinically relevant range. Lower numbers of scans may also be suitable such as ≥16 scans, particularly depending on the relevant clinical decision levels and/or curve fitting performance. Currently, the LoQ of the 128 scan assay is close to the $25^{th}$ percentile (2.43 µM) and the LoQ for the 96 scan assay is close to the $50^{th}$ percentile (3.67 µM). Given the biological variability and the fact that a current medical decision point is at the 75th percentile (6.18 µM), a 96 scan assay may be sufficient. This data is plotted as the % CV versus concentration. The data are fit with a simple power function as indicated on the plot and, from this, concentration yielding a 20% CV is calculated. This value is the accepted value for the LoQ. Concentrations below the LoQ cannot currently be quantitatively reported with a high degree of confidence (but may be qualitatively reported). The values shown in FIGS. 12A and 12B may change as the assay is optimized.

The biosample can comprise any suitable pH-buffer alone or with other buffers as noted above. The buffer(s) can be present with a buffer to serum or plasma ratio of any one of the following (or any number there between) 10:90, 15:85; 20:80, 25:75, 30:70; 35:65, 40:60, 45:55, 50:50 and even 60:40 (or other values where there is more buffer or buffers than sample). However, embodiments of the invention use more sample by volume than buffers or other additives, e.g., reference or calibration additives. In certain embodiments, a buffer can maximize the amount serum or plasma in the biosample (e.g., provide a buffer to serum or plasma ratio of 45:55 or greater). In some particular embodiments, the sample comprises a 25:75 (buffer:serum) sample composition that is easy to prepare and provides a significant increase in sensitivity over a 50:50 composition. It is contemplated that, in some embodiments, low volume biosamples may be analyzed, such as ≤50 µL. If so, it may be suitable to formulate the biosample to have a greater amount of buffer relative to serum or other biospecimen (e.g., saliva, CSF) such as, for example, 75:25 (buffer:biospecimen).

A buffer can include one or more of albumin, glucose, citrate, acetate or other acidic compounds as well any of the well established chemical shift or quantitation references such as formate, trimethylsilylpropionate (and isotopically labeled isomers), and EDTA for example.

Exemplary pH buffers include, but are not limited to, acidic buffers, such as, but not limited to, a citrate, a phosphate, and/or an acetate buffer. For example, the biosample can comprise a citrate buffer and/or citrate phosphate buffer having a pH from about 2.6 to about 5.5 and comprising citric acid, sodium citrate, and/or sodium phosphate. Other exemplary buffers include, but are not limited to, an acetate buffer and/or an acetate phosphate buffer having a pH from about 3.7 to about 5.5 and comprising acetic acid, sodium acetate, and/or sodium phosphate. In some embodiments, the biosample comprises a citrate phosphate buffer comprising citric acid and sodium dibasic phosphate. Typically, the buffers are mixed with deionized water and are added to the biosample to dilute the sample by a defined amount. However, the chemical buffer(s) may also be added directly into a liquid or tissue biosample.

In some embodiments, the biosample comprises a citrate phosphate buffer comprising citric acid monohydrate and sodium dibasic phosphate heptahydrate. Citric acid monohydrate can be present in a citrate phosphate buffer in an amount from about 160 mM to about 170 mM, or any range therein, such as, but not limited to, about 164 mM to about 167 mM, about 164.4 mM to about 165.6 mM, or about 165.6 mM to about 166.7 mM. Sodium dibasic phosphate heptahydrate can be present in a citrate phosphate buffer in an amount from about 260 mM to about 275 mM, or any range therein, such as, but not limited to, about 267 mM to about 272 mM, about 267.2 mM to about 269.6 mM, or about 269.6 mM to about 271.9 mM. In some embodiments, citrate phosphate buffer can comprise about 160 mM to about 170 mM citric acid and about 260 mM to about 275 mM sodium dibasic phosphate heptahydrate. In certain embodiments, the biosample comprises a citrate phosphate buffer comprising about 165.6 mM citric acid monohydrate, about 269.6 mM sodium dibasic phosphate heptahydrate, and deionized water. In some embodiments, a citrate phosphate buffer has a pH of about 4.65.

The sample may be prepared for analysis shortly before analysis by the NMR spectrometer (manually or automatically with a sample handler) or at a remote, pre-processing or collection site. For example, a TMAO analysis container can be pre-loaded with the amount and or processed for analysis. In other embodiments, the collection container itself can be pre-loaded with the buffer in a range and the container marked for sample collection level to form the desired buffer: serum volume so that the appropriate amount of biosample is collected in the container.

FIGS. 13A and 13B are graphs assessing the accuracy of the assay by comparing values from gravimetric measure of TMAO into spiked dialyzed serum versus NMR and NMR versus MS determined TMAO in patient samples. The agreement of NMR in both graphs is acceptable with R2 values greater than 0.9.

Figure 14A:
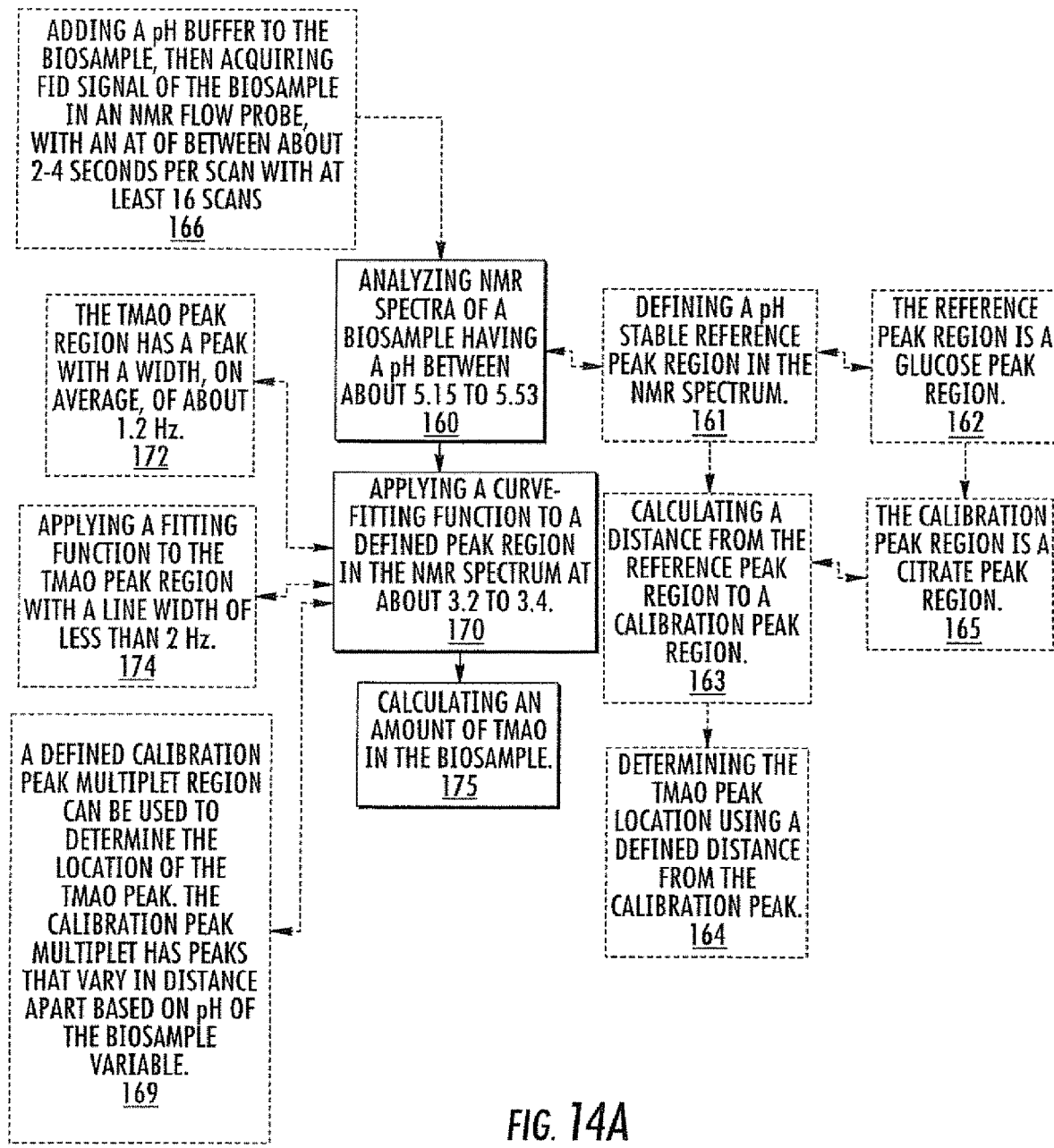
FIG. 14A is a flow chart of exemplary operations that can be used to carry out embodiments of the invention.

FIG. 14A is a flow chart of exemplary operations that can be used to carry out embodiments of the present invention. NMR spectra of a biosample having a pH between about 5.15 to 5.53 are electronically analyzed (block 160). A curve-fitting function (that can selectively apply one or more of a plurality of predefined basis functions to use zero, one, two or three neighboring peaks) can be applied to a defined peak region in the NMR spectrum at about 3.2 to 3.4 (block 170). An amount of TMAO in the biosample is calculated (block 175).

In some embodiments, a defined pH stable reference peak region in the NMR spectrum can be identified (block 161). A distance from the reference peak region to a calibration peak region can be calculated (block 163). The TMAO peak location can be determined using a defined distance from the calibration peak (block 164).

The reference peak region can be a (anomeric) glucose peak region (block 162).

In some embodiments, a defined calibration peak multiplet region can be used to determine the location of the TMAO peak. The calibration peak multiplet has peaks that vary in distance apart based on pH of the biosample variable (block 169).

The calibration peak region can be a citrate peak region (block 165).

The method may include adding a pH buffer to the biosample, then acquiring FID signal of the sample in an NMR flow probe (166) with an AT of less than about 4 seconds per scan with a plurality of scans per biosample. The TMAO peak region can have a peak with a width, on average, of about 1.2 Hz (block 172) (and can vary to be between about 0.6 Hz and 2 Hz per biosample). A fitting function can be applied to the TMAO peak region with a line width of under 2 Hz, typically about 1 Hz (block 174).

The position of a TMAO peak region can be calculated using a fitting region having a size between 50-100 data points based on a location of a citrate reference peak or peaks, then reducing the fitting region to about 30-50 data points centered about the calculated location of the TMAO peak. TMAO peak region can be analyzed with a defined curve fitting function or functions that can selectively allow for one or more neighbors on either side to account for small misalignments to determine the level of TMAO.

As noted above, the probable actual TMAO peak location can be identified by weighting the region around the expected TMAO peak location with a Gaussian, triangular parabolic or similar function. The probable actual TMAO peak location can then be identified as the highest weighted data point used to center the curve fitting region for determining the level of TMAO.

Figure 14B:
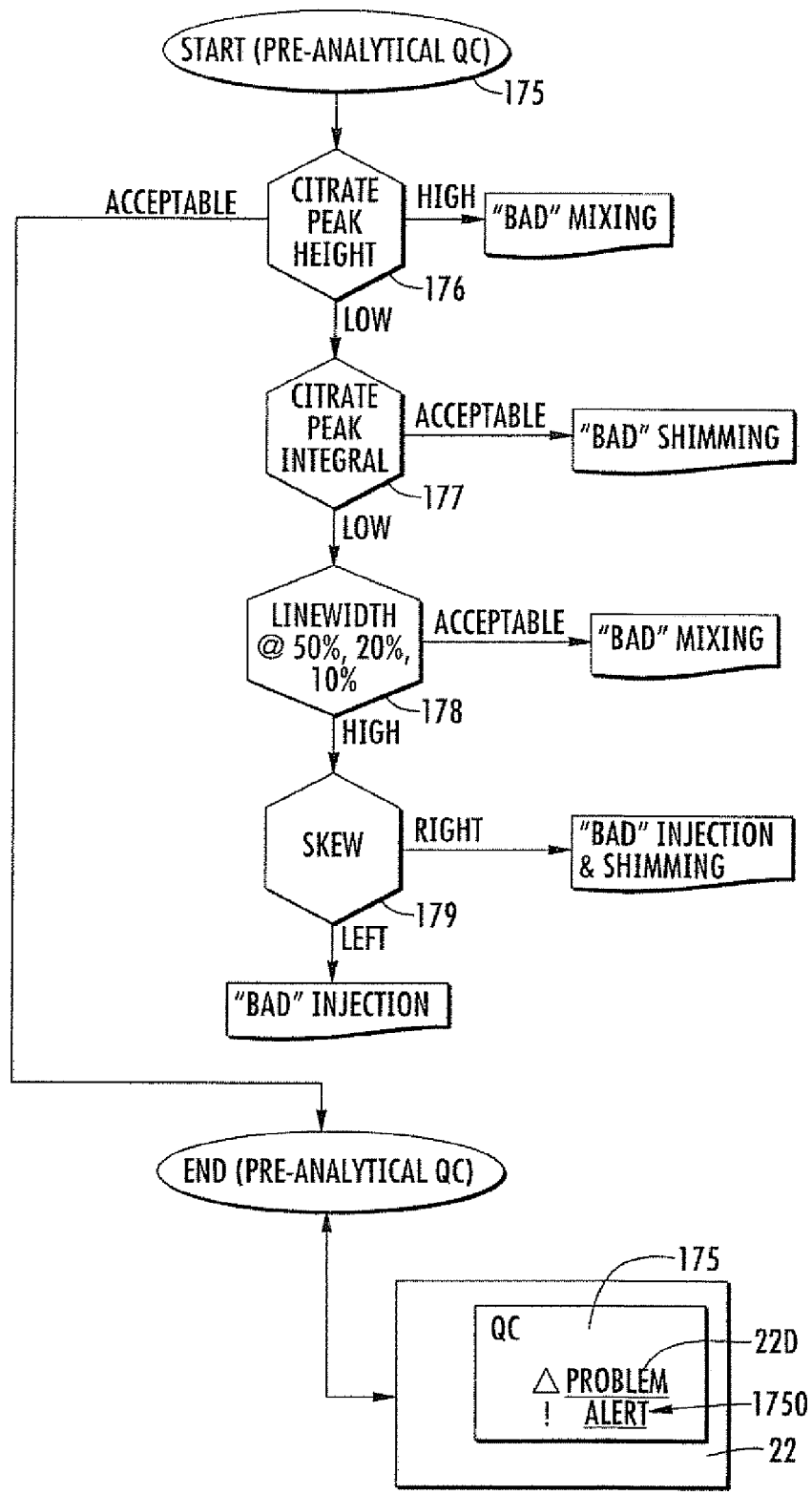
FIG. 14B is a flow chart of an exemplary pre-analytical quality control evaluation that can be carried out according to embodiments of the present invention.
Figure 14C:
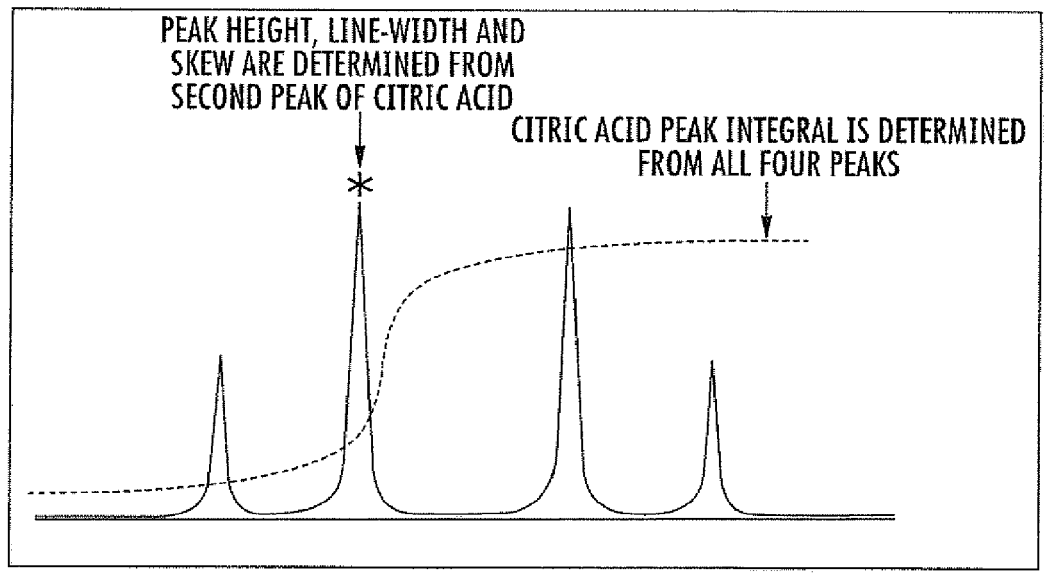
FIG. 14C is a multiplet (reference) peak region of an NMR spectrum that can be used for the quality control evaluation shown in FIG. 14B according to embodiments of the present invention.
Figure 14D:
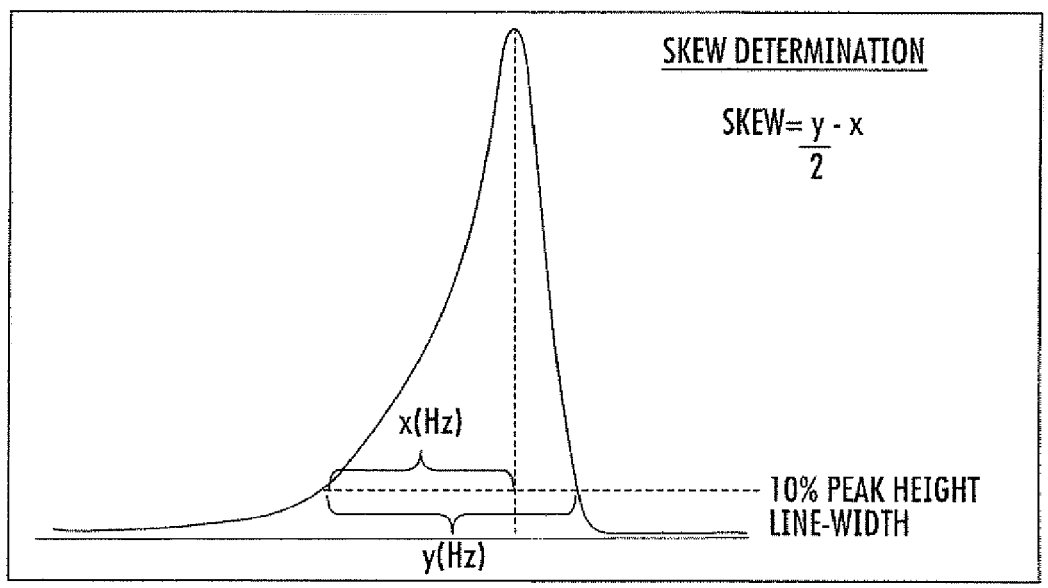
FIG. 14D is an enlarged view of one peak shown in FIG. 14C that can be used to evaluate skew according to embodiments of the present invention.

FIGS. 14B, 14C and 14D illustrate an exemplary (and optional) automated pre-analytical quality control evaluation 175 that can be carried out programmatically (e.g., by the analyzer 22 or a processor in communication with the analyzer 22) before performing a clinical assay, e.g., the TMAO assay according to some embodiments. Thus, the TMAO assay is not performed if the input spectra fail pre-analytical quality control checks. The pre-analytical quality control evaluation 175 evaluates input spectra to determine acquisition occurred or will occur under specified conditions:

Sample is properly mixed and the injected sample completely fills the flow cell
Magnetic field is homogeneous
Water suppression is adequate
Sample pH is within a defined range, e.g., 5.3±0.1.

Evaluation of these conditions is based on characterization of a reference peak in the spectra. In the case of the TMAO assay, the citrate peak serves as the pH sensitive reference peak. The height, integral, linewidth and skew of one of the citrate peaks is evaluated. This information is used as shown in the flowchart shown in FIG. 14B to identify problems with mixing, injection and shimming.

As shown in FIG. 14B, a reference peak height is evaluated (shown as citrate) block 176. For ease of discussion, the term "citrate" will be used for this evaluation, but other reference peaks may also be used. If it is high, this indicates "bad mixing" or too much serum. If low, the citrate peak integral is obtained (block 177). If the integral is acceptable (within defined values), this indicates "bad" shimming and can alert an operator via an output 175o (audio and visual or just visual) on the display 22D to initiate a shim operation or generate an alert that identifies the problem. If low, a linewidth is taken at 50%, 20% and 10% (block 178), if acceptable, this indicates "bad mixing" associated with the sample and again the analyzer 22 can alert an operator of the problem or flag via an output on the display 22D and/or initiate a retest. If high, skew can be evaluated (block 179). If it is right of a defined location, a "bad injection and bad shimming" alert can be generated to the operator (e.g., via display 22D) and if it is to the left, only a "bad injection alert is generated.

The programmatic evaluation 175 can determine the following characteristics of the reference (e.g., citrate peak or peaks) for each input spectra. Height of one of the citric acid peaks, typically the second peak from the left (marked with asterisk * in FIG. 14C) can be determined. Linewidth of one peak, typically the second citric acid peak from the left at 50%/20%/10% peak height (FIG. 14D) and the integral of all four citric acid peaks (FIG. 14C) can be determined. Skew can be determined at 10% of second citric acid peak from the left using skew=y/2−x (FIG. 14D).

Bad shimming can identified if the citrate height is <97 au and has an acceptable citrate peak integral between 3674 and 3314 for any of the input spectra. The low height indicates that the peak is too broad indicating poor field homogeneity.

Bad mixing can be identified if the citrate height is <97 au, citrate integral <3314 au, acceptable line-width of <1.65/3.15/4.74 Hz (at 50%/20%/10% peak height, respectively) for any of the input spectra. Other threshold values may be appropriate under different sample and/or data acquisition conditions.

Bad injection or bad shimming can be identified if the citrate height is <97 au, citrate integral <3314 au, the line-widths are >1.65/3.15/4.74 Hz (at 50%/20%/10% peak height, respectively), and 10% skew is to the right more than +0.09 to +0.32 Hz for any of the input spectra. Other threshold values may be appropriate under different sample and/or data acquisition conditions Bad injection can be identified if the citrate height is <97 au, citrate integral <3314 au, the line-widths are >1.65/3.15/4.74 Hz (at 50%/20%/10% peak height, respectively), and 10% skew is to the left more than −0.09 to −0.32 Hz for any of the input spectra. Other threshold values may be appropriate under different sample and/or data acquisition conditions It is noted that the flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

Figures 15A, 15B:
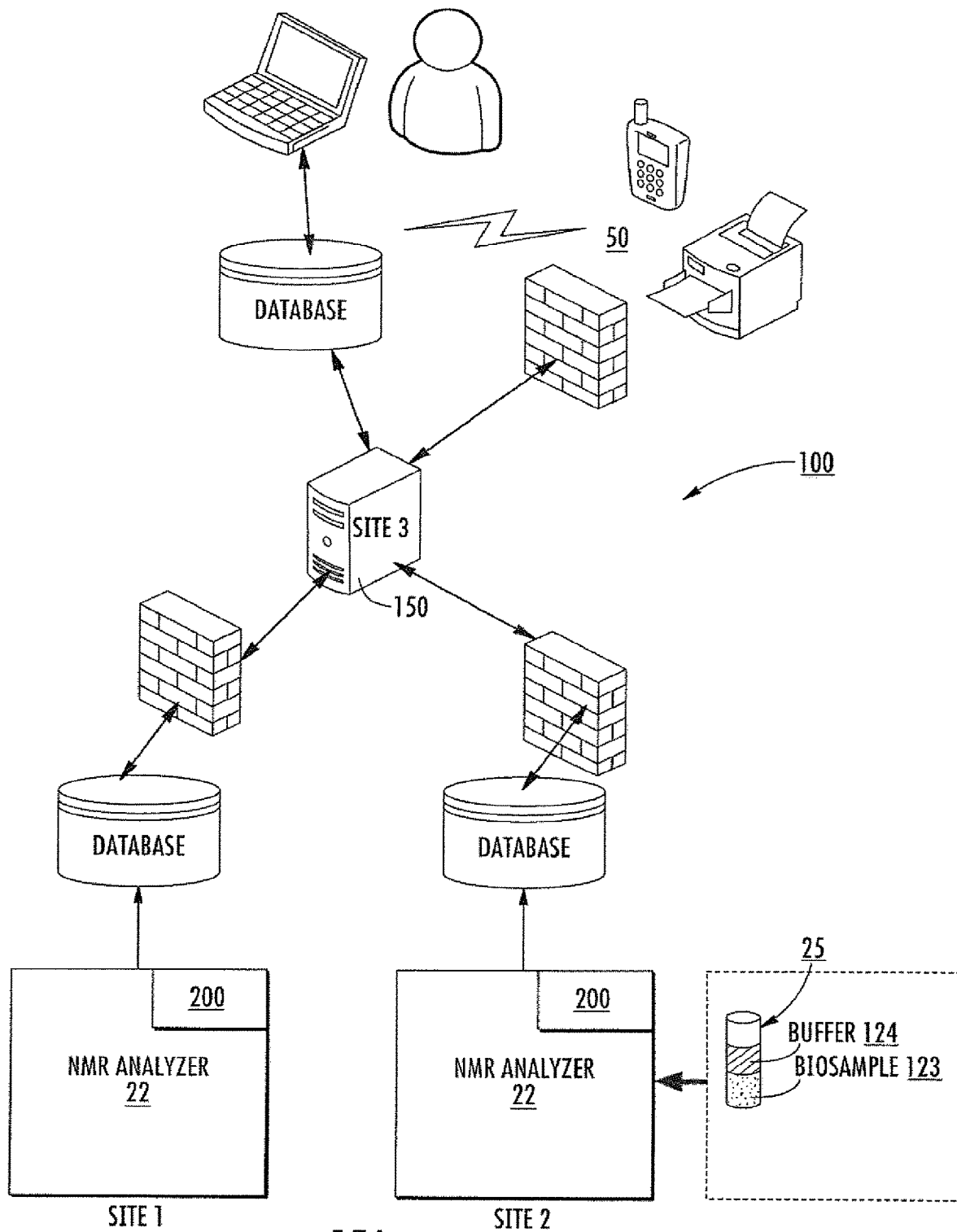
FIG. 15A is a schematic illustration of an NMR measurement system according to embodiments of the present invention.
FIG. 15B is a schematic illustration of a container with a patient sample and buffer solution for analysis to assess TMAO level according to embodiments of the present invention.

Referring now to FIG. 15A, it is contemplated that the TMAO analysis can be carried out using a system 100 with at least one NMR clinical analyzer 22 as described, for example, with respect to FIG. 15B below and/or in U.S. Pat. No. 8,013,602, the contents of which are hereby incorporated by reference as if recited in full herein.

The system 100 can include a NMR TMAO analysis module and/or circuit 200 that can be onboard the analyzer 22 or at least partially remote from the analyzer 22. If the latter, the analysis module or circuit 200 can reside totally or partially on a server 150. The server 150 can be provided using cloud computing which includes the provision of computational resources on demand via a computer network. The resources can be embodied as various infrastructure services (e.g. computer, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers. Data transfer can be encrypted and can be done via the Internet using any appropriate firewalls to comply with industry or regulatory standards such as HIPAA. The term "HIPAA" refers to the United States laws defined by the Health Insurance Portability and Accountability Act. The patient data can include an accession number or identifier, gender, age and test data.

As shown in FIG. 15B, the at least one analyzer 22 can be configured to evaluate containers 25 of biosamples 123 optionally including one or more defined diluents or buffers 124. The containers 25 can have sample/buffer solutions and may be flowably introduced to the NMR probe using a flow cell or the containers can be placed in the NMR probe for evaluation. The containers 25 can include respective biosamples of human blood plasma or serum with a solution of citrate acid and sodium dibasic phosphate in a defined ratio, the ratio being between 25:75 to about 50:50 (buffer:serum) by volume, with the pH being between about 5.15 and 5.53.

The results of the analysis can be transmitted via a computer network, such as the Internet, via email or the like to a patient, clinician site 50, to a health insurance agency or a pharmacy. The results can be sent directly from the analysis site (Site 1, Site 2) or may be sent indirectly via a central or distributed network (Site 3). The results may be printed out and sent via conventional mail. This information can also be transmitted to pharmacies and/or medical insurance companies, and/or respective patients. The results can be sent to a patient via email to a "home" computer or to a pervasive computing device such as a smart phone or notepad and the like. The results can be as an email attachment of the overall report or as a text message alert, for example.

The systems can be configured to measure different biosamples for assessing TMAO levels. For example, both urine and blood samples can be analyzed and measurements reported together or separately with any associated risk or as an independent measurement.

Figure 16:
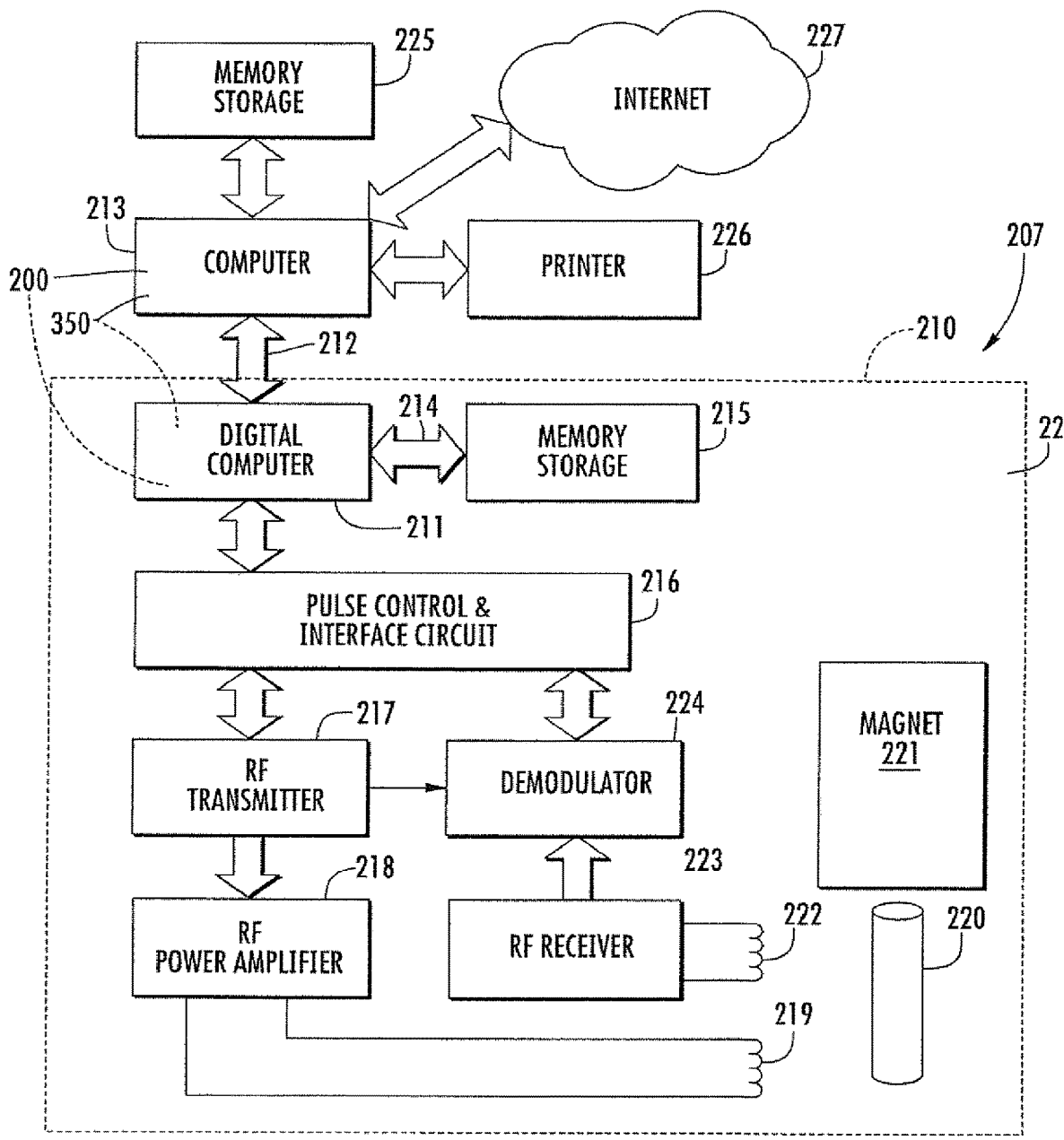
FIG. 16 is a schematic illustration of an NMR analyzer according to embodiments of the present invention.

Referring now to FIG. 16, a system 207 for acquiring and calculating the lineshape of a selected sample is illustrated. The system 207 includes an NMR spectrometer 22 for taking NMR measurements of a sample. In one embodiment, the spectrometer 22 is configured so that the NMR measurements are conducted at about 400 MHz for proton signals; in other embodiments the measurements may be carried out at between 200-900 MHz or other suitable frequency. Other frequencies corresponding to a desired operational magnetic field strength may also be employed. Typically, a proton flow probe is installed, as is a temperature controller to maintain the sample temperature at about 47+/−0.5 degrees C. However, as noted above, other sample temperatures may be employed. The spectrometer 22 is controlled by a digital computer 214 or other signal processing unit. The computer 211 should be capable of performing rapid Fourier transformations. It may also include a data link 212 to another processor or computer 213, and a direct-memory-access channel 214 which can connects to a hard memory storage unit 215.

The digital computer 211 may also include a set of analog-to-digital converters, digital-to-analog converters and slow device I/O ports which connect through a pulse control and interface circuit 216 to the operating elements of the spectrometer. These elements include an RF transmitter 217 which produces an RF excitation pulse of the duration, frequency and magnitude directed by the digital computer 211, and an RF power amplifier 218 which amplifies the pulse and couples it to the RF transmit coil 219 that surrounds sample cell 220. The NMR signal produced by the excited sample in the presence of a 9.4 Tesla polarizing magnetic field produced by superconducting magnet 221 is received by a coil 222 and applied to an RF receiver 223. The amplified and filtered NMR signal is demodulated at 224 and the resulting quadrature signals are applied to the interface circuit 216 where they are digitized and input through the digital computer 211. The TMAO analyzer circuit 200 and/or module 350 (FIGS. 15A and 17) can be located in one or more processors associated with the digital computer 211 and/or in a secondary computer 213 or other computers that may be on-site or remote, accessible via a worldwide network such as the Internet 227.

The TMAO analyzer circuit 200 can include a database of experimental determinations of concentrations of TMAO to curves and/or areas of TMAO peak regions for different levels of expected TMAO values in biologic ranges as is known to those of skill in the art. Reference standards can be used for calibration or defining concentrations of NMR measurements. The TMAO experimental or reference samples can be obtained from known suppliers of "high purity" TMAO material (e.g., Sigma-Aldrich, LLC.). The TMAO analyzer circuit 200 can include a TMAO basis function that accounts for the residual protein baseline interferences that may survive the pulse sequence (e.g., the CPMG pulse sequence). The TMAO basis function can be an experimentally acquired spectrum of TMAO processed with defined (consistent) parameters to the actual spectrum. Computationally derived TMAO basis functions may also be used (e.g., specified Lorentzians, Gaussians or mixed functions) or combinations of same.

After the NMR data are acquired from the biosample in the measurement cell 220, processing by the computer 211 produces another file that can, as desired, be stored in the storage database 215. This second file is a digital representation of the chemical shift spectrum and it is subsequently read out to the computer 213 for storage in its storage 225 or a database associated with one or more servers. Under the direction of a program stored in its memory, or in another database or circuit in communication with the NMR analyzer 22 (or spectrometer), one or more processors, such as one associated with the computer 213, which may be a personal, laptop, desktop, workstation, notepad, tablet or other computer, processes the chemical shift spectrum in accordance with the teachings of the present invention to generate a report which may be output to a printer 226 or electronically stored and relayed to a desired server, database(s), email address or URL. Those skilled in this art will recognize that other output devices, such as a computer display screen, notepad, smart phone and the like, may also be employed for the display of results.

It should be apparent to those skilled in the art that the functions performed by the computer 213 and its separate storage 225 may also be incorporated into the functions performed by the spectrometer's digital computer 211. In such case, the printer 226 may be connected directly to the digital computer 211. Other interfaces and output devices may also be employed, as are well-known to those skilled in this art.

Embodiments of the present invention may take the form of an entirely software embodiment or an embodiment combining software and hardware aspects, all generally referred to herein as a "circuit" or "module."

As will be appreciated by one of skill in the art, the present invention may be embodied as an apparatus, a method, data or signal processing system, or computer program product. Accordingly, the present invention may take the form of an entirely software embodiment, or an embodiment combining software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java7, Smalltalk, Python, Labview, C++, or VisualBasic. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN), a wide area network (WAN), a secure area network (SAN) or the connection may be made to an external computer (for example, through the Internet using an Internet Service Provider).

Figure 17:
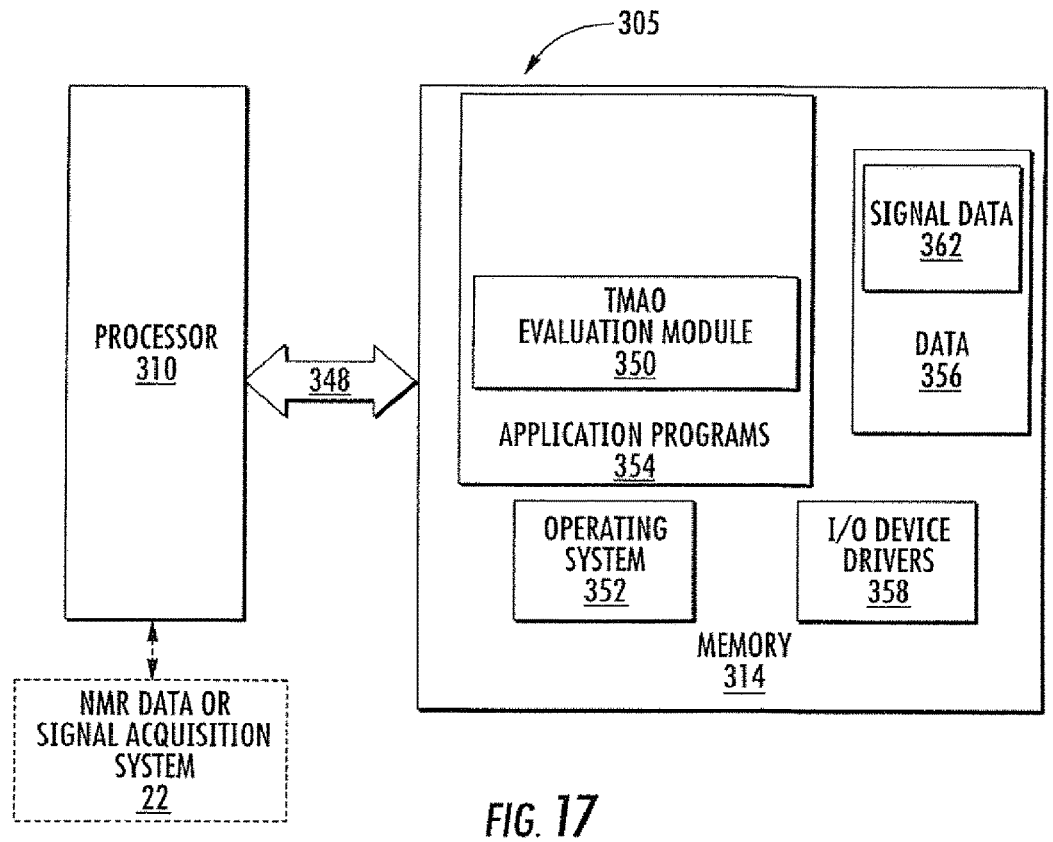
FIG. 17 is a block diagram of a data processing system according to embodiments of the present invention.

FIG. 17 is a block diagram of exemplary embodiments of data processing systems that illustrates systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 17, the memory 314 may include several categories of software and data used in the data processing system 305: the operating system 352; the application programs 354; the input/output (I/O) device drivers 358; a TMAO Evaluation Module 350; and the data 356. The TMAO Evaluation Module 350 can interrogate one or more defined NMR signal peak regions in proton NMR spectra of a respective biosample to identify a level of TMAO. As noted above, the TMAO Evaluation Module 350 may identify a reference peak region (pH stable) and a calibration peak region (pH variable) to more precisely locate the TMAO peak region based on a predetermined relationship of distance between the calibration, reference and TMAO peak regions. In some particular embodiments, the TMAO Module 350 can also subtract a known TMAO standard concentration from a calculated concentration of the TMAO based on the amount of TMAO standard added to the biosample to amplify the TMAO peak.

The data 356 may include signal (constituent and/or composite spectrum lineshape) data 362 which may be obtained from a data or signal acquisition system 320. As will be appreciated by those of skill in the art, the operating system 352 may be any operating system suitable for use with a data processing system, such as OS/2, AIX or OS/390 from International Business Machines Corporation, Armonk, N.Y., WindowsCE, WindowsNT, Windows95, Windows98, Windows2000 or WindowsXP from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 358 typically include software routines accessed through the operating system 352 by the application programs 354 to communicate with devices such as I/O data port(s), data storage 356 and certain memory 314 components and/or the image acquisition system 320. The application programs 354 are illustrative of the programs that implement the various features of the data processing system 305 and can include at least one application, which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the Module 350 being an application program in FIG. 17, as will be appreciated by those of skill in the art, other configurations may also be utilized while still benefiting from the teachings of the present invention. For example, the TMAO Module 350 may also be incorporated into the operating system 352, the I/O device drivers 358 or other such logical division of the data processing system 305. Thus, the present invention should not be construed as limited to the configuration of FIG. 17, which is intended to encompass any configuration capable of carrying out the operations described herein.

In certain embodiments, the Module 350 includes computer program code for providing a level of TMAO which may be used to assess CHD risk and/or to indicate whether therapy intervention is desired and/or track efficacy of a therapy. The TMAO test may be used in conjunction with clinical evaluation and other diagnostic tests as an aid in assessing a patients risk for developing cardiovascular disease (CVD) or coronary heart disease (CHD).

The NMR evaluated TMAO can be a useful companion diagnostic t nutritional guidance in the use of prebioticprobiotic containing foods or supplements or other types of functional foods.

TMAO may also provide valuable information for other clinical applications including therapeutic monitoring and/or management. TMAO measurements can be used for management associated with specific diet, probiotic or drug treatment(s). TMAO measurements can be used with clinical trials and/or drug development programs. The TMAO measurements can be used to contradict a planned or actual therapy.

TMAO may be used to monitor for signs or diagnosis of kidney transplant rejection. Metabolic profiling evaluations of kidney transplants have revealed biomarkers that include altered levels of trimethylamine-N-oxide (TMAO), dimethylamine, lactate, acetate and alanine. In many of these investigations, TMAO was increased by a factor of 3-4 compared to healthy controls. The increase in TMAO is believed to stabilize proteins when there is an increased concentration of protein denaturants such as urea and guanidine derivatives following a toxic insult to the kidney.

TMAO measurements may also be used to evaluate patients having Trimethylaminuria (TMAU), also known as fish odor syndrome or fish malodor syndrome. TMAU is a rare metabolic disorder that causes a defect in the normal production of the enzyme Flavin containing monooxygenase 3 (FMO3). When FMO3 is not working correctly or if not enough enzyme is produced, the body loses the ability to convert trimethylamine (TMA) from precursor compounds in food digestion into trimethylamine oxide (TMAO) through a process called N-oxygenation. Trimethylamine then builds up and is released in the person's sweat, urine, and breath, giving off a strong fishy odor or strong body odor. Measurement of urine for the ratio of trimethylamine to trimethylamine oxide is the standard screening test.

Figure 18:
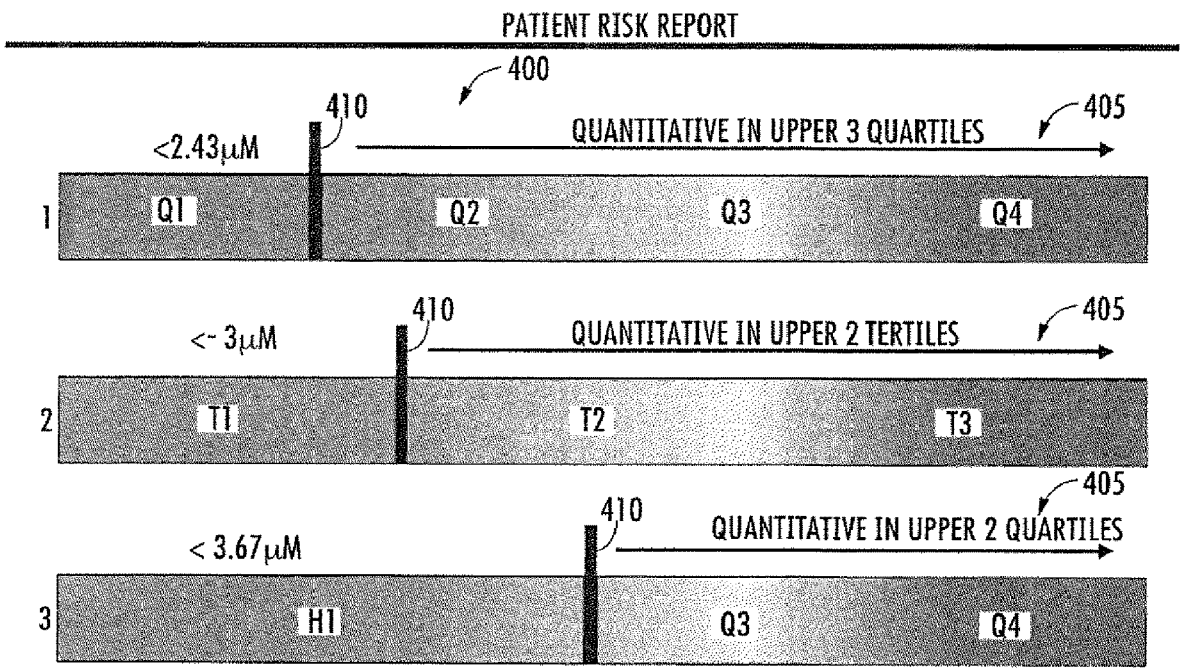
FIG. 18 is a schematic illustration of a patient report with examples of visual risk indicia associated with different levels of TMAO according to embodiments of the present invention.

FIG. 18 illustrates patient reports 400 that may include visual indicia of risk 405 associated with TMAO measurements. FIG. 18 illustrates three potential embodiments of the TMAO risk report dependent upon the lower limit of quantitation that is achievable due to analytical consideration and/or what is appropriate based on biological variability, particularly associated with blood plasma or serum samples.

The visual indicia 405 can include a graphic with a degree of risk indicated in a defined color scale. The color scale may range from "green", "yellow" and "red or orange" for a continuum of risk from low (green) to higher risk (red/orange). The red or orange is indicated by the cross-hatch markings while the yellow is shown by the lighter gray scale. Green or another low risk color can be used for the Q1, T1 or H1 (lower half) values. Other colors may be used to visually denote risk. The report 400 may be generated with quantitative results only for the upper 3 quartiles, the upper two tertiles or the upper 2 quartiles. As shown in the three exemplary visual risk indicia formats, a demarcation line 410 can separate the lower range values from the upper ranges. In other embodiments, a quantitative result can be provided for all quartiles or tertiles of measurements.

Figure 19:
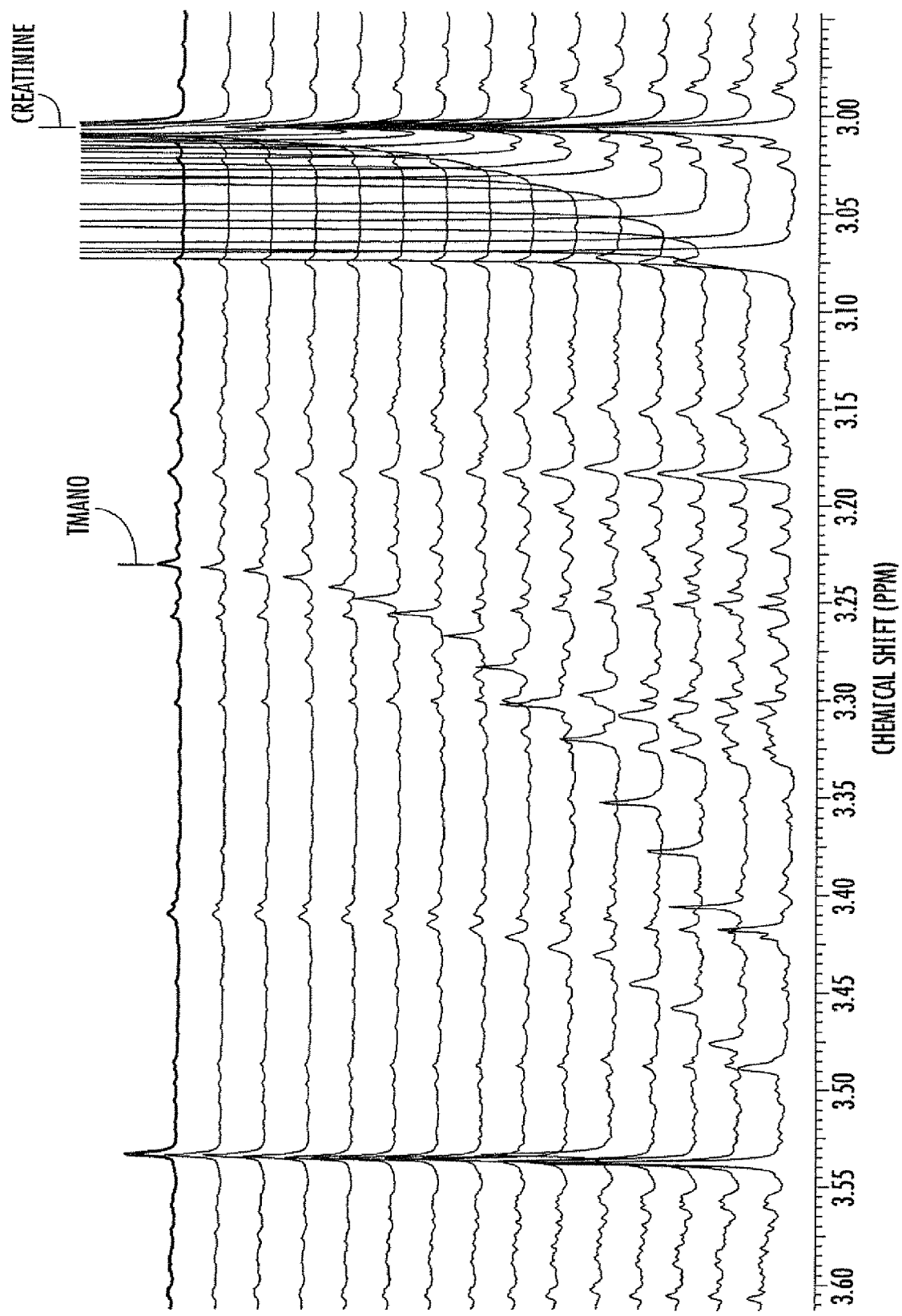
FIG. 19 is a stacked plot of NMR spectra (chemical shift/ppm) of urine according to embodiments of the present invention (the pH goes from 4.62 at the bottom to 6.83 at the top).
Figure 20A:
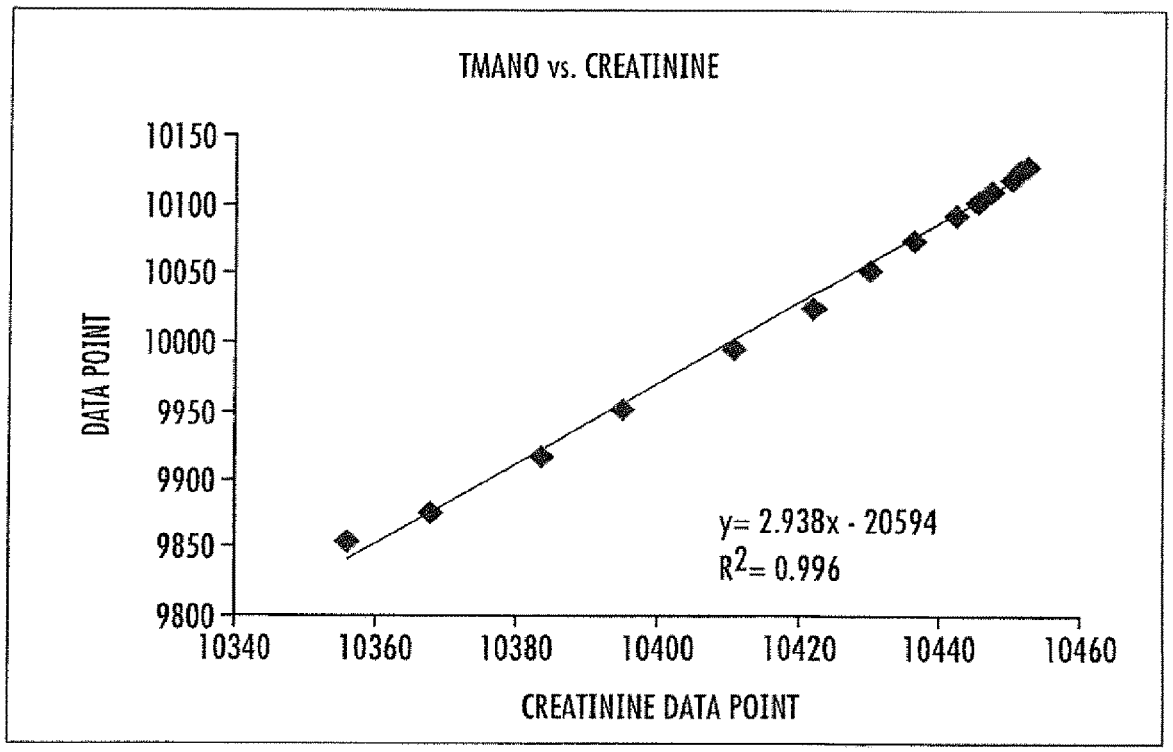
FIGS. 20A and 20B are graphs of a TMAO peak versus reference peak (FIG. 20A shows Creatinine and FIG. 20B shows Citrate) illustrating a relationship between TMAO and the reference peak according to embodiments of the present invention.
Figure 20B:
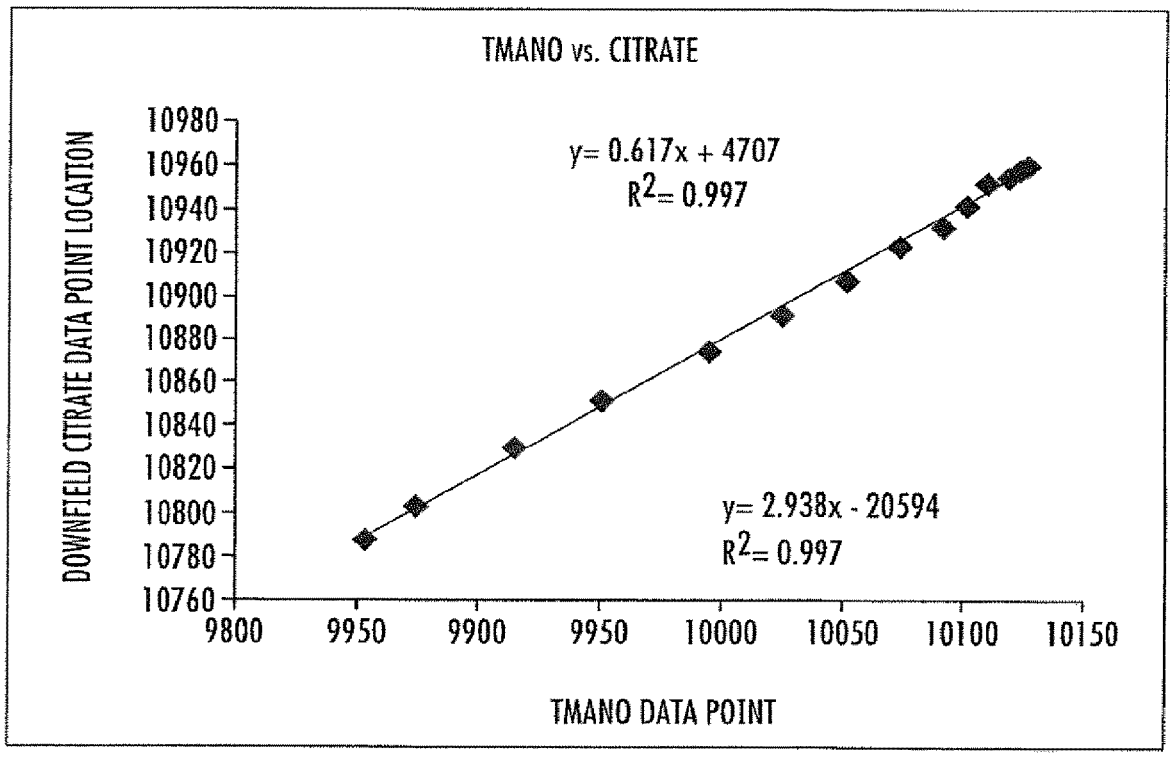

FIG. 19 is an NMR (chemical shift/ppm) spectrum of urine according to embodiments of the present invention. The urinary TMAO concentration is typically much higher than in serum, but the range is quite large. Urine is also in a "crowded" matrix and there is a large number of potentially confounding metabolites. As in the serum matrix, adjustment of the pH can be used to move the TMAO peak into more or less crowded regions. FIG. 19 illustrates an expansion of the TMAO region of a $^1$H NMR spectrum of urine. The samples were prepared with a 60:40 mixture of urine and NMR diluent with the pH starting at 4.62 at the bottom and going to 6.83 in the top; pH step size is approximately 0.15 units.

The location of the TMAO peak can be reliably determined by using either (or both) the creatinine peak labeled in the FIG. 19 or the citrate peak. Both creatinine and citrate are endogenous metabolites in urine and so this pH referencing could be carried out without the addition of corresponding compounds in the buffer or diluent. The relationship between the TMAO peak location and the respective citrate and creatinine peak locations are show in FIGS. 20A and 20B. Both graphs show a nearly linear correlation between the TMAO and the respective potential reference peak. It is noted that the exact nature of the relationship between the TMAO peak location and the creatinine and citrate can be dependent upon the sample composition, i.e., ratio of urine to buffer.

Quantitation of the TMAO concentration of the urine and other biosamples (e.g., blood plasma and serum) can be achieved by modeling the TMAO signal with computationally derived functions. The baseline can be modeled by DC offset, linear, and/or quadratic functions. The TMAO peak can be modeled by Lorentzian and/or Gaussian functions of varying line widths. These "mixed" basis set functions can have the identical height (FIG. 21) or be normalized by area (FIG. 22).

Figure 21:
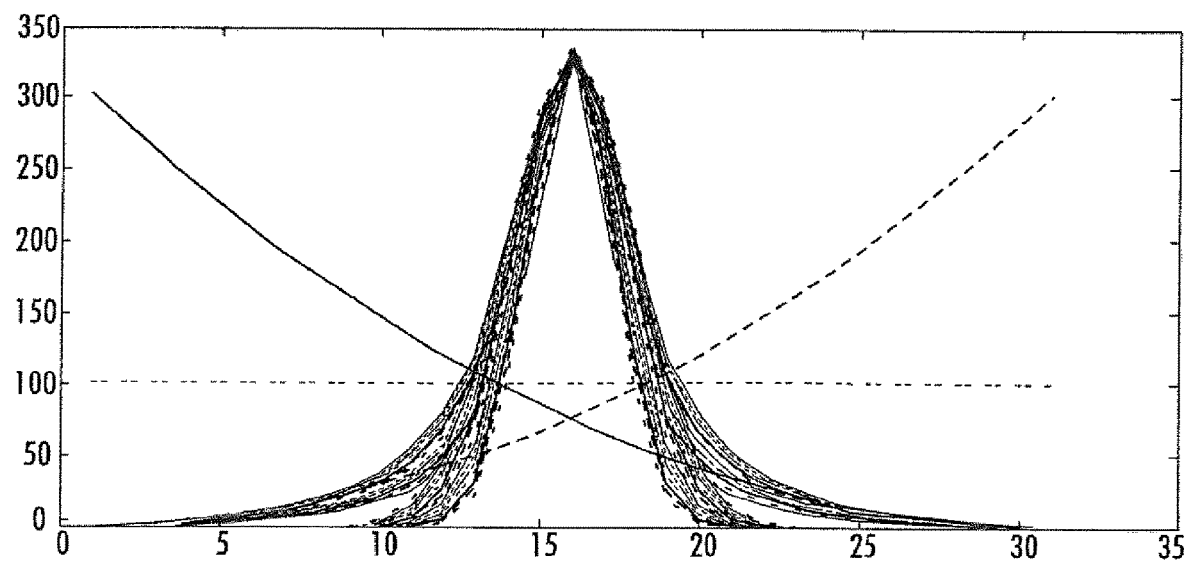
FIG. 21 is a graph of a series of Lorentzian and Gaussian basis functions used to model the TMAO signal to determine TMAO concentration according to embodiments of the present invention.

FIG. 21 shows a basis set of Lorentzian and Gaussian functions to model TMAO signal. The height of each function is identical. DC offset and quadratic functions can be used to model baseline signal.

Figure 22:
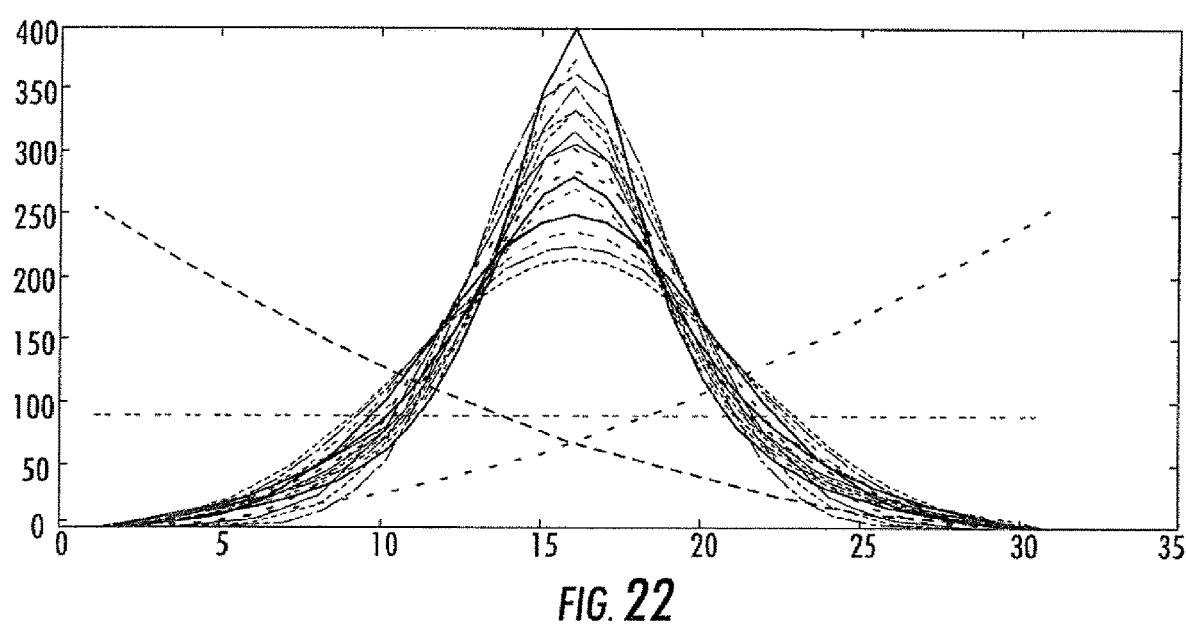
FIG. 22 is a graph of a series of Lorentzian and Gaussian basis functions used to model baseline TMAO signal to determine TMAO concentration according to embodiments of the present invention. These basis functions have constant area but have differential peak heights and linewidths.

FIG. 22 shows a normalized basis set of Lorentzian and Gaussian functions to model TMAO signal. The area of each function is identical. DC offset and quadratic functions used to model baseline signal are also normalized to the same area.

Figure 23:
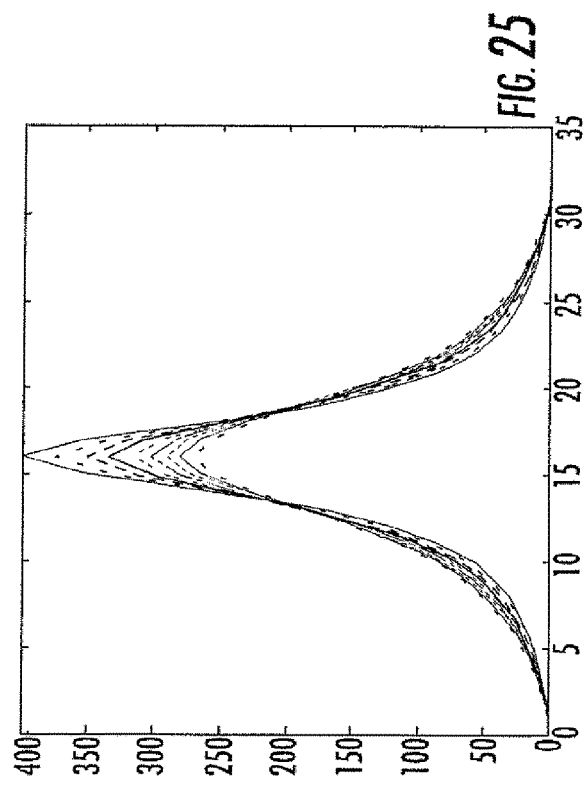
FIGS. 23-26 are graphs of additional examples of basis sets (Lorentzian alone, FIGS. 23, 25 and Gaussian alone, FIGS. 24, 26) according to embodiments of the present invention.
Figure 24:
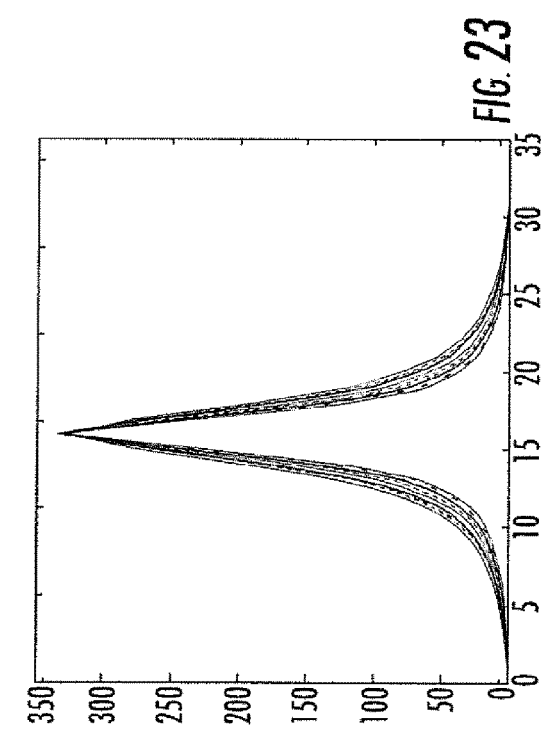
Figure 25:
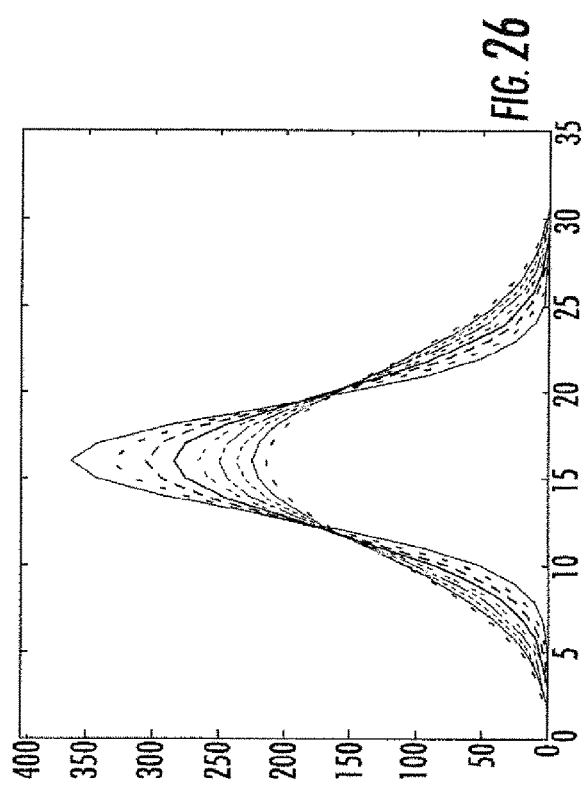
Figure 26:
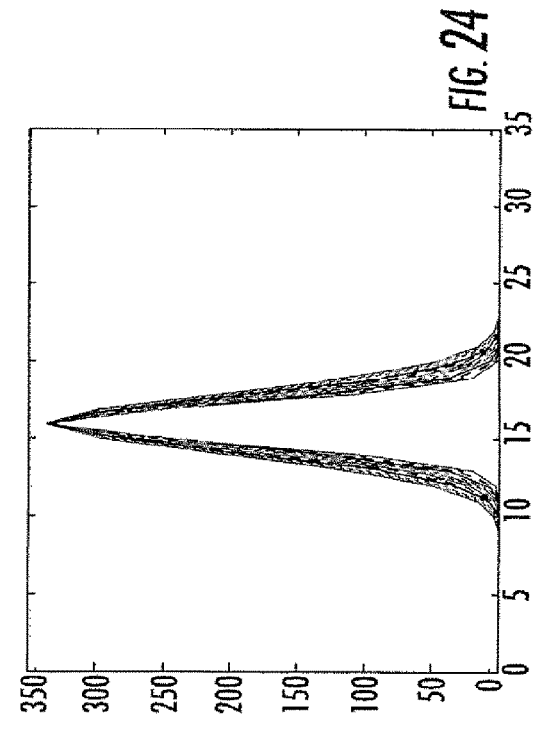

FIGS. 23-26 are graphs of additional examples of basis sets. FIG. 23 shows Lorentzian functions with identical height and varying line width. FIG. 24 shows Gaussian functions with identical height and varying line width. FIG. 25 shows Lorentzian functions with normalized area and varying line width. FIG. 26 shows Gaussian functions with normalized area and varying line width.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of determining a measure of TMAO in in vitro biosamples, comprising:

calibrating NMR measurements for trimethylamine-N-oxide ("TMAO") by identifying a location of a pH-stable reference peak and using a defined linear relationship between the location of the pH-stable reference peak and a location of a pH-sensitive calibration peak;
generating a proton NMR spectrum for an in vitro biosample; and
electronically determining a level of TMAO in the in vitro biosample using a defined TMAO peak region having a single TMAO peak residing between about 3.2 and 3.4 ppm of the proton NMR spectrum, wherein the level of TMAO is in a range of 1 µM to 50 µM, and
wherein the calibration peak is electronically identified in a defined calibration peak region in the proton NMR spectrum of the biosample.

2. The method of claim 1, further comprising:
electronically calculating a distance between the reference and calibration peak regions; and
electronically determining a location of the TMAO peak for the defined TMAO peak region based on the calculated distance.

3. The method of claim 1, wherein the biosample comprises blood, plasma, or serum, wherein the defined TMAO peak is at about 3.30 ppm.

4. The method of claim 3, wherein the biosample further comprises urine, wherein the level of TMAO in urine is in a range of 0-1000 µM.

5. The method of claim 1, further comprising:
electronically identifying a defined calibration peak multiplet with peaks that can vary in distance apart from one another based on pH of the biosample;
determining at least one distance between one or more of the peaks in the calibration peak multiplet; and
electronically determining a pH of the biosample based on the at least one determined distance;
wherein the electronically determining the location of the TMAO peak for the defined TMAO peak region is carried out based on the determined pH and/or the at least one distance between peaks in the calibration multiplet.

6. The method of claim 1, further comprising, before the electronically determining step, electronically calculating a location of the defined TMAO peak region using a fitting region having a size between about 50-100 data points based on a location of the pH-stable reference peak or pH-sensitive calibration peak or peaks, then reducing the fitting region to about 30 data points centered about the calculated location of the defined TMAO peak region, and electronically curve fitting the defined TMAO peak region with a defined curve fitting function or functions to determine the level of TMAO.

7. The method of claim 1, wherein the electronic determination of the level of TMAO is carried out using a defined relationship between a location of the pH-stable reference peak or peaks and a location of the pH-sensitive calibration peak or peaks, and an expected TMAO peak location, wherein a probable actual TMAO peak location is then identified by:
electronically weighting a region around the expected TMAO peak location with a defined function; then
electronically identifying a highest weighted data point of the weighted region; and then
electronically identifying a probable actual TMAO peak location corresponding to location of the highest weighted data point.

8. The method of claim 7, wherein after the identification of the probable actual TMAO peak location, the method further comprises applying a curve fitting function or functions to a curve fitting region of about 30 to about 50 data points centered about the identified probable actual TMAO peak location to determine the level of TMAO.

9. The method of claim 8, wherein the curve fitting function or functions can selectively allow for one or more neighbors on either side of the probable actual TMAO peak location to account for misalignments to determine the level of TMAO.

10. One or more processors configured to evaluate in vitro biosamples, the processor configured to:
calibrate NMR measurements for trimethylamine-N-oxide ("TMAO") by identifying a location of a pH-stable reference peak and using a defined linear relationship between the location of the pH-stable reference peak and a location of a pH-sensitive calibration peak;
generate a proton NMR spectrum for an in vitro biosample; and
electronically determine NMR signal in at least one defined peak region that includes a TMAO peak region residing between about 3.2 and 3.4 ppm of a proton NMR spectrum of an in vitro biosample to determine a level of TMAO,
wherein the calibration peak is electronically identified in a defined calibration peak region in the NMR spectrum of the biosample, and wherein the level of TMAO is in a range of 1 µM to 50 µM.

11. The one or more processors of claim 10, wherein the one or more processors are further configured to:
identify a pH-stable reference peak region in the proton NMR spectrum of the biosample;
identify a defined calibration peak region in the proton NMR spectrum of the biosample;
identify a distance between the pH-stable reference peak and pH-sensitive calibration peak regions; and
determine a position of the TMAO peak region based on a calculated reference and calibration peak region distance.

12. The one or more processors of claim 11, wherein determining the position of the TMAO peak region employs a defined mathematical relationship of a location of the pH-stable reference peak to a location of the pH-sensitive calibration peak and the location of the pH-sensitive calibration peak to a location of the TMAO peak, and wherein the calibration and TMAO peak region locations vary according to pH of the biosample.

13. The one or more processors of claim 11, wherein the pH-stable reference peak region comprises a glucose peak region and the pH-sensitive calibration peak region comprises one or more peaks of a citrate peak multiplet.

14. The one or more processors of claim 13, wherein the glucose peak region comprises an anomeric glucose proton peak centered at about 5.20 ppm, and wherein the one or more peaks of the citrate peak multiplet are centered at about 3.7 ppm.

15. The one or more processors of claim 10, wherein the one or more processors are further configured to:
calculate a position of the TMAO peak region using a fitting region having first size between about 50-100 data points based on a location of the pH-stable reference peak or pH- sensitive calibration peak or peaks;
reduce the fitting region to about 30 data points centered about a calculated location of the TMAO peak region; and apply a defined curve fitting function or functions to signal associated with the TMAO peak region.

16. A system comprising the one or more processors of claim 10 and at least one NMR spectrometer for acquiring at least one proton NMR spectrum of an in vitro biosample.

17. A method of monitoring patients for therapeutic treatment, comprising:
  electronically determining a level of trimethylamine-N-oxide ("TMAO") in an in vitro biosample from a subject using a defined TMAO peak region having a single TMAO peak residing between about 3.2 and 3.4 ppm of a proton NMR spectrum; and
  administering a prebiotic, probiotic, or drug to a patient for treatment of kidney transplant rejection or fish odor syndrome based on the level of TMAO in the biosample.

18. The method of claim 17, wherein the biosample comprises blood, plasma, or serum, wherein the level of TMAO in blood, plasma, or serum is in a range of 1 to 50 µM.

19. The method of claim 18, wherein the biosample further comprises urine, wherein the level of TMAO in urine is in a range of 0-1000 µM.

\* \* \* \* \*